United States Patent [19]
Mewshaw et al.

[11] Patent Number: 6,110,956
[45] Date of Patent: Aug. 29, 2000

[54] N-ARYLOXYETHYLAMINE DERIVATIVES FOR THE TREATMENT OF DEPRESSION

[75] Inventors: Richard E. Mewshaw, Princeton; Dahui Zhou, Highland Park; Ping Zhou, Plainsboro, all of N.J.

[73] Assignee: American Home Products Corp., Madison, N.J.

[21] Appl. No.: 09/287,416

[22] Filed: Apr. 7, 1999

Related U.S. Application Data

[60] Provisional application No. 60/093,052, Apr. 8, 1998.

[51] Int. Cl.[7] .................. A61K 31/404; A61K 31/4045; A61P 25/24; C07D 209/04; C07D 403/08
[52] U.S. Cl. .................. 514/415; 514/414; 514/429; 548/305.1; 548/306.1; 548/490; 548/517; 548/518; 548/525; 548/526
[58] Field of Search .................. 514/414, 415, 514/429; 548/490, 517, 518

[56] References Cited

U.S. PATENT DOCUMENTS

| | | | |
|---|---|---|---|
| 3,371,098 | 2/1968 | Kralt et al. | 260/326.14 |
| 5,436,264 | 7/1995 | Pfister et al. | 514/415 |
| 5,468,767 | 11/1995 | Cipollina et al. | 514/414 |

FOREIGN PATENT DOCUMENTS

| | | |
|---|---|---|
| 20722941 | 7/1996 | European Pat. Off. . |
| 5125024 | 5/1993 | Japan . |
| 5255302 | 10/1993 | Japan . |
| 9040648 | 2/1997 | Japan . |
| WO9808817 | 3/1998 | WIPO . |
| WO9808819 | 3/1998 | WIPO . |

OTHER PUBLICATIONS

Le Poul et al., *Arch. Pharmacol.*, 352:141 (1995).
Artigas et al., *Trends Neurosci.*, 19:378–383 (1996).

*Primary Examiner*—Joseph McKane
*Assistant Examiner*—Jane C. Osweicki
*Attorney, Agent, or Firm*—Michael R. Nagy

[57] ABSTRACT

Compounds effective in treating disorders of the serotonin-affected neurological systems are provided, such compounds having the following formula:

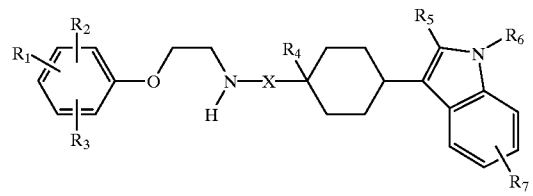

wherein:

$R_1$ and $R_2$ are each, independently, hydrogen, halogen, $CF_3$, lower alkyl, lower alkoxy, $MeSO_2$, or together can form a 5–7 membered carbocyclic or heterocyclic ring;

$R_3$ is alkoxy, halogen, hydrogen or carbamoyl;

$R_4$ is hydrogen, hydroxy, lower alkyl, or lower alkoxy;

$R_5$ is hydrogen, lower alkyl, or halogen;

$R_6$ is hydrogen, lower alkyl, or phenyl;

$R_7$ is hydrogen, lower alkyl, lower alkoxy, halogen, CN, $CF_3$, or hydroxy; and X is $(CH_2)_n$, wherein n is 0 to 3; or pharmaceutically acceptable salts thereof.

35 Claims, No Drawings

N-ARYLOXYETHYLAMINE DERIVATIVES FOR THE TREATMENT OF DEPRESSION

CROSS REFERENCE TO RELATED APPLICATIONS

This application claims the benefit of U.S. Provisional Application Ser. No. 60/093,052, which was converted from U.S. patent application Ser. No. 09/057,307, filed Apr. 8, 1998, pursuant to a petition filed under 37 C.F.R. 1.53(c)(2)(i) filed Jul. 30, 1998.

FIELD OF INVENTION

This invention relates to useful for the treatment of diseases affected by disorders of the serotonin-affected neurological systems. More specifically, the present invention is directed to N-aryloxyethylarnine derivatives useful for the treatment of such disorders.

BACKGROUND OF INVENTION

Pharmaceuticals which enhance neurotransmission of serotonin (5-HT) are useful for the treatment of many psychiatric disorders, including depression and anxiety. The first generation of non-selective serotonin-affecting drugs operated through a variety of physiological means which caused them to possess numerous undesired side effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. As SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of the 5-HT neurons, causing a dampening of the therapeutic effect. Studies suggest that after several weeks of SSRI administration, a desensitization of the 5-HT autoreceptors occurs allowing a full antidepressant effect in most patients (See, e.g., Le Poul et al., *Arch. Pharmacol.* 352:141 (1995)). Hence, it is believed that overriding this negative feedback by using 5HT1A antagonists would potentially increase and accelerate the clinical antidepressant response. Recent studies by Artigas et al., *Trends Neurosci.,* 19:378–383, (1996) suggest that a combination of 5-HT1A activity and inhibition of 5-HT uptake within a single molecular entity can achieve a more robust and fast-acting antidepressant effect.

The present invention relates to a new class of molecules which have the ability to act at the 5-HT1A autoreceptors and concommitantly with the 5-HT transporter. Such compounds are therefore potentially useful for the treatment of depression as well as other serotonin disorders.

U.S. Pat. No. 3,371,098 discloses sec. and tert. indolylethylamines useful as sedatives, anticonvulsants and analgesics.

U.S. Pat. No. 5,436,264 discloses N-aryloxyalkyltryptamine-like compounds of the following formula as alpha-1-adrenergic receptor antagonists for the treatment of cardiovascular disorders.

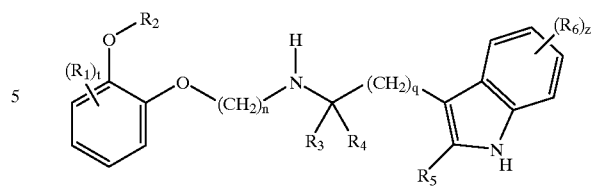

European Patent No. 0722 941 A2 discloses the preparation of a series of the following hetero-oxy alkanamines of formula for the treatment of depression and other conditions for which serotonin uptake inhibitors are normally used.

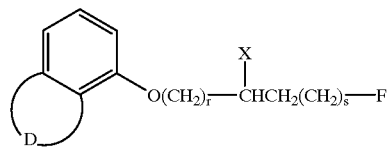

Japanese Patent Nos. 05255302 and 09040648 disclose the following compounds which are reported to be useful for the treatment of central nervous system-related diseases such as anxiety and depression.

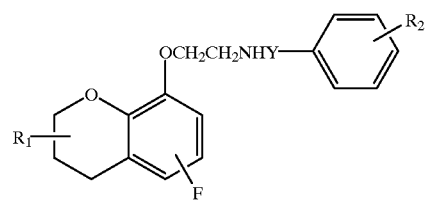

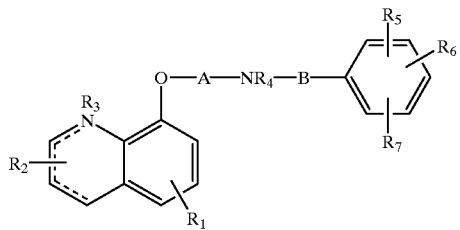

U.S. Pat. No. 5,468,767 discloses a series of substituted indoles of the following formula for the treatment of disorders associated with dysfunction in serotonergic neurotrnsmission, including depression.

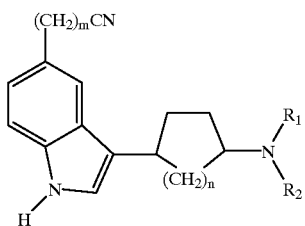

SUMMARY OF THE INVENTION

The compounds of the present invention are N-aryloxyethylamines represented by Formula I:

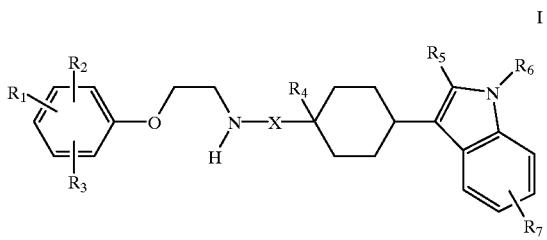

wherein
- $R_1$ and $R_2$ are each, independently, hydrogen, halogen, $CF_3$, lower alkyl, lower alkoxy, $MeSO_2$, or together can form a 5–7 membered carbocyclic or heterocyclic ring;
- $R_3$ is alkoxy, halogen, hydrogen or carbamoyl;
- $R_4$ is hydrogen, hydroxy, lower alkyl, or lower alkoxy;
- $R_5$ is hydrogen, lower alkyl, or halogen;
- $R_6$ is hydrogen, lower alkyl, or phenyl;
- $R_7$ is hydrogen, lower alkyl, lower alkoxy, halogen, CN, $CF_3$, or hydroxy; and
- X is $(CH_2)_n$, wherein n is 0 to 3; or pharmaceutically acceptable salts thereof.

DETAILED DESCRIPTION OF THE INVENTION

Preferably, the compounds of the present invention are those of Formula I wherein:
- $R_1$ and $R_2$ are each, independently, lower alkyl, lower alkoxy, halogen, or together can form a 5–7 membered carbocyclic or heterocyclic ring;
- $R_3$ is alkoxy, halogen, hydrogen or carbamoyl;
- $R_4$ is hydrogen or hydroxy;
- $R_5$ is hydrogen;
- $R_6$ is hydrogen, or lower alkyl;
- $R_7$ is halogen or CN; and
- X is $(CH_2)_n$, wherein n is 0–3; or pharmaceutically acceptable salts thereof.

Most preferably, the compounds of the present invention are selected from the following:

[(cis)-4-(5-Fluoro-1H-indol-3-yl)-cyclohexyl]-[2-2-methoxy-phenoxy)-ethyl]-amine;
[(trans)-4-(5-Fluoro-1H-indol-3-yl)-cyclohexyl]-[2-(2-methoxy-phenoxy)-ethyl]-amine;
[(1,4-cis)-4-(6-Fluoro-1H-indol-3-yl)-cyclohexyl]-[2-(5-fluoro-2-methoxy-phenoxy)-ethyl]amine;
[(1,4-trans)-4-(6-Fluoro-1H-indol-3-yl)-cyclohexyl]-[2-(5-fluoro-2-methoxy-phenoxy)-ethyl]-amine;
[(cis)-4-(5-Fluoro-1H-indol-3-yl)-cyclohexyl]-[2-(2-(1H-indol-4-yloxy)ethyl]-amine;
[(trans)-4-(5-Fluoro-1H-indol-3-yl)-cyclohexyl]-[2-(2-(1H-indol-4-yloxy)ethyl]-amine;
[(cis)-4-(1H-Indol-3-yl)-cyclohexyl]-[2-(2-(1H-indol-4-yloxy)ethyl]-amine;
[(trans)-4-(1H-Indol-3-yl)-cyclohexyl]-[2-(2-(1H-indol-4-yloxy)ethyl]-amine;
[2-(2,3)-Dihydro-benzo[1,4]dioxin-5-yloxy-ethyl]-[(1,4-cis)-4-(5-fluoro-1H-indol-3-yl)-cyclohexyl]-amine;
[2-(2,3)-Dihydro-benzo[1,4]dioxin-5-yloxy-ethyl]-[(1,4-trans)-4-(5-fluoro-1H-indol-3-yl)-cyclohexyl]amine;
[2-(2,3)-Dihydro-benzo[1,4]dioxin-5-yloxy-ethyl]-[(1,4-cis)-4-(6-fluoro-1H-indol-3-yl)-cyclohexyl]-amine;
[2-(2,3)-Dihydro-benzo[1,4]dioxin-5-yloxy)-ethyl]-[(1,4-trans)-4-(6-fluoro-1H-indol-3-yl)-cyclohexyl]-amine;
[2-(6-Fluorochroman-8-yloxy)-ethyl]-[(1,4-cis)-4-(5-fluoro-1H-indol-3-yl)-cyclohexyl]-amine;
[2-(6-Fluorochroman-8-yloxy)-ethyl]-[(1,4-trans)-4-(5-fluoro-1H-indol-3-yl)-cyclohexyl]-amine;
3-{(1,4-cis)-4-[2-(6-Fluorochroman-8-yloxy)-ethylamino]-cyclohexyl}-1-methyl-1H-indol-5-carbonitrile;
3-{(1,4-cis)-4-[2-(6-Fluorochroman-8-yloxy)-ethylamino]-cyclohexyl}-1-methyl-1H-indol-5-carbonitrile;
3-{(1,4-trans)-4-[2-(6-Fluorochroman-8-yloxy)-ethylamino]-cyclohexyl}-1H-indol-5-carbonitrile;
3{(1,4-cis)-4-[2-(5-Fluoro-2,3-dihydro-benzofuran-7-yloxy)ethylamino]-cyclohexyl]}-1H-indol-5-carbonitrile;
3-{(1,4-trans)-4-[2-(5-Fluoro-2,3-dihydro-benzofuran-7-yloxy)ethylamino]-cyclohexyl}-1H-indol-5-carbonitrile;
[2-(5-Fluoro-benzofuran-7-yloxy)-ethyl]-[(1,4-cis)-4-(5-fluoro-1H-indol-3-yl)-cyclohexyl]-amine;
[2-(5-Fluoro-benzofuran-7-yloxy)-ethyl]-[(1,4-trans)-4-(5-fluoro-1H-indol-3-yl)-cyclohexyl]-amine;
[2-(6-Chloro-1H-benzoimidazol-4-yloxy)-ethyl]-[(1,4-trans)-4-(5-fluoro-1H-indol-3-yl)-cyclohexyl]-amine;
[2-(6-Chloro-2-methyl-1H-benzoimidazol-4-yloxy)-ethyl]-[(1,4-trans)-4-(5-fluoro-1H-indol-3-yl)-cyclohexyl]-amine;
[(1,4-cis)-4-(5-Fluoro-1H-indol-3-yl)-cyclohexyl]-[2-(4-fluoro-2-methoxy-phenoxy)-ethyl]-amine;
[(1,4-trans)-4-(5-Fluoro-1H-indol-3-yl)-cyclohexyl]-[2-(4-fluoro-2-methoxy-phenoxy)-ethyl]-amine;
[(1,4-trans)-4-(5-Fluoro-1H-indol-3-yl)-cyclohexylmethyl]-[2-(2-methoxy-phenoxy)-ethyl]-amine;
3-(4-{[2-(methoxy-phenoxy)-ethylamino]-methyl}-cyclohexyl)-1H-indol-5-carbonitrile;
(1,4-cis)-[2-(4,5-Difluoro-2-methoxy-phenoxy)-ethyl]-{4-(5-fluoro-1H-indol-3-yl)-cyclohexyl]-amine;
(1,4-trans)-[2-(4,5-Difluoro-2-methoxy-phenoxy)-ethyl]-[4-(5-fluoro-1H-indol-3-yl)-cyclohexyl]-amine;
[(1,4-trans)-4-(5-Fluoro-1H-indol-3-yl)-cyclohexyl]-[2-(5-fluoro-4-methanesulfonyl-2-methoxy-phenoxy)-ethyl]-amine; and
(1,4)-4-(5-Fluoro-1H-indol-3-yl)-1-{[2-(1H-indol-4-yloxy)-ethylamino]-methyl}-cyclohexanol.

As used herein, the terms "lower alkyl" and "lower alkoxy" are meant to include both straight and branched carbon chains containing 1 to 6 carbon atoms. The term "halogen" is meant to include fluorine, chlorine, bromine, and iodine.

The compounds of this Formula I may advantageously be used in the form of the pharmaceutically acceptable acid addition salts thereof. Such salts, prepared by methods well known to those skilled in the art, are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzenesulfonic, hydrochloric hydrobromic, sulfuric, cyclohexylsulfamic, phosphoric and nitric acids.

The compounds of the present invention may be prepared by any suitable method which will be recognized by those skilled in the art. However, the present compounds may be advantageously prepared according to any one of Schemes 1–12 set forth below. In the Schemes, the intermediate compounds exemplified hereinafter are identified in parenthesis. The compound produced in each of Schemes 1–12 is identified with reference to the appropriate Example set forth below.
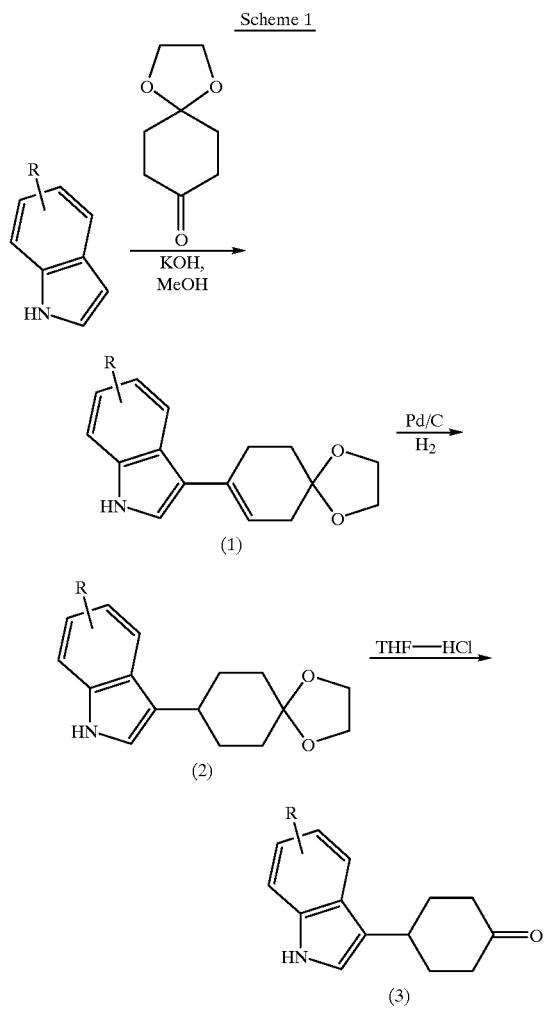
Where R = 5-F, 6-F, or 5-CN
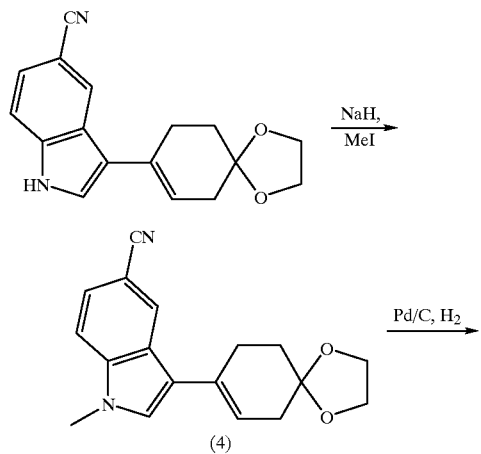
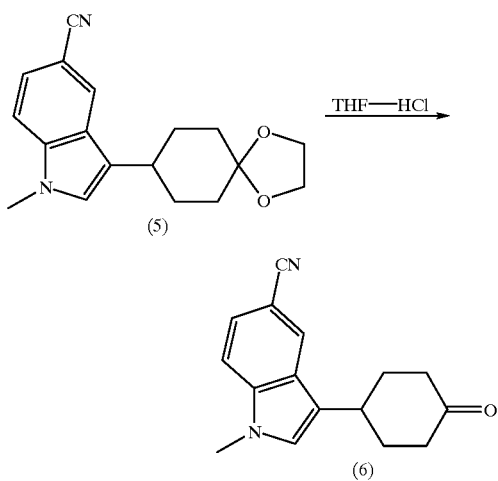
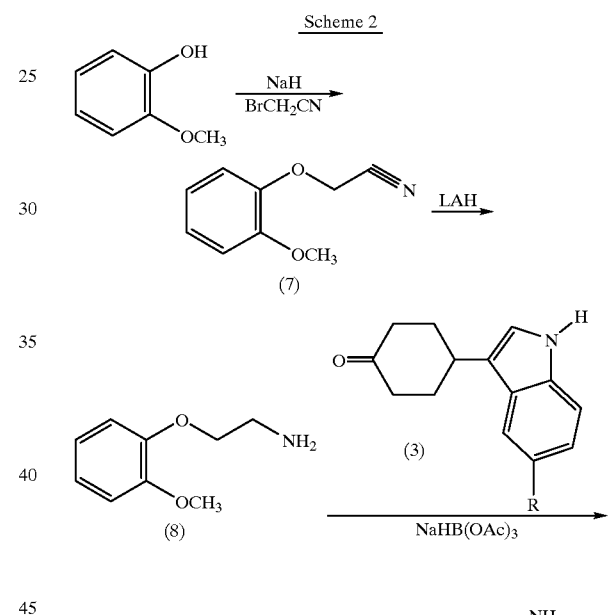
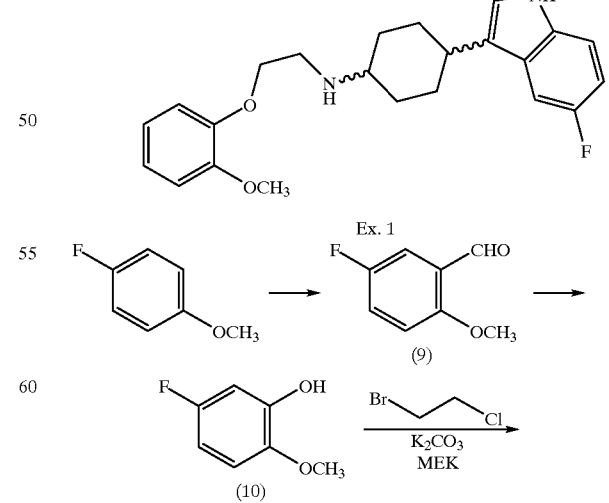

-continued
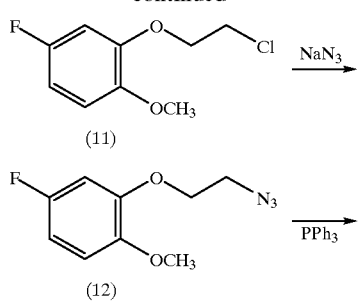
(11)
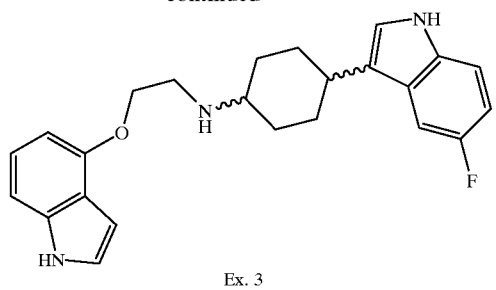
Ex. 3
(12)
Scheme 4
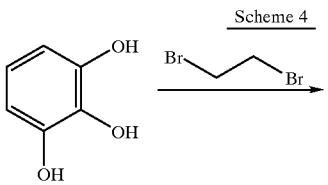
(13)
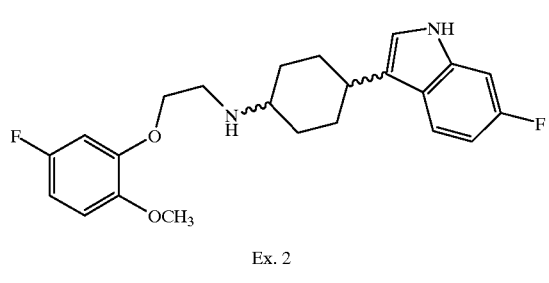
Ex. 2
(16)
(17)
Scheme 3
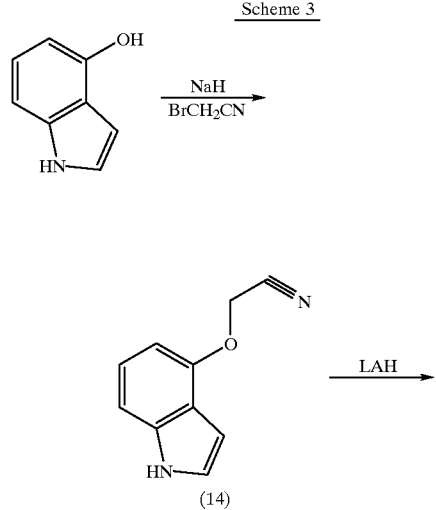
(14)
(18)
(19)
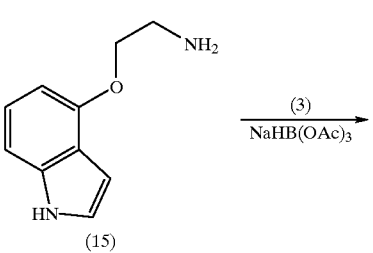
(15)
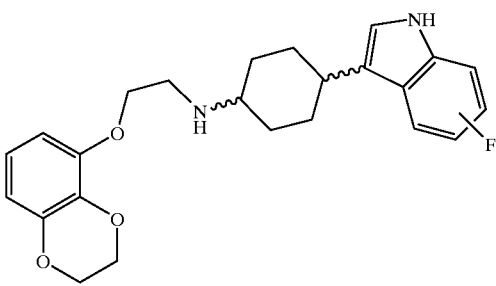
Ex. 4

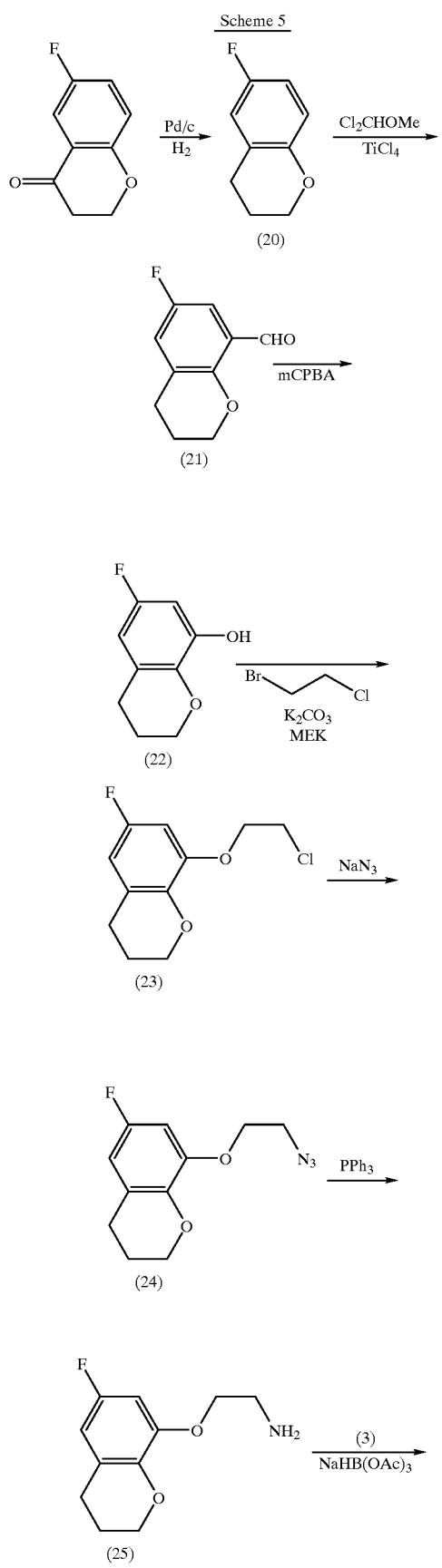
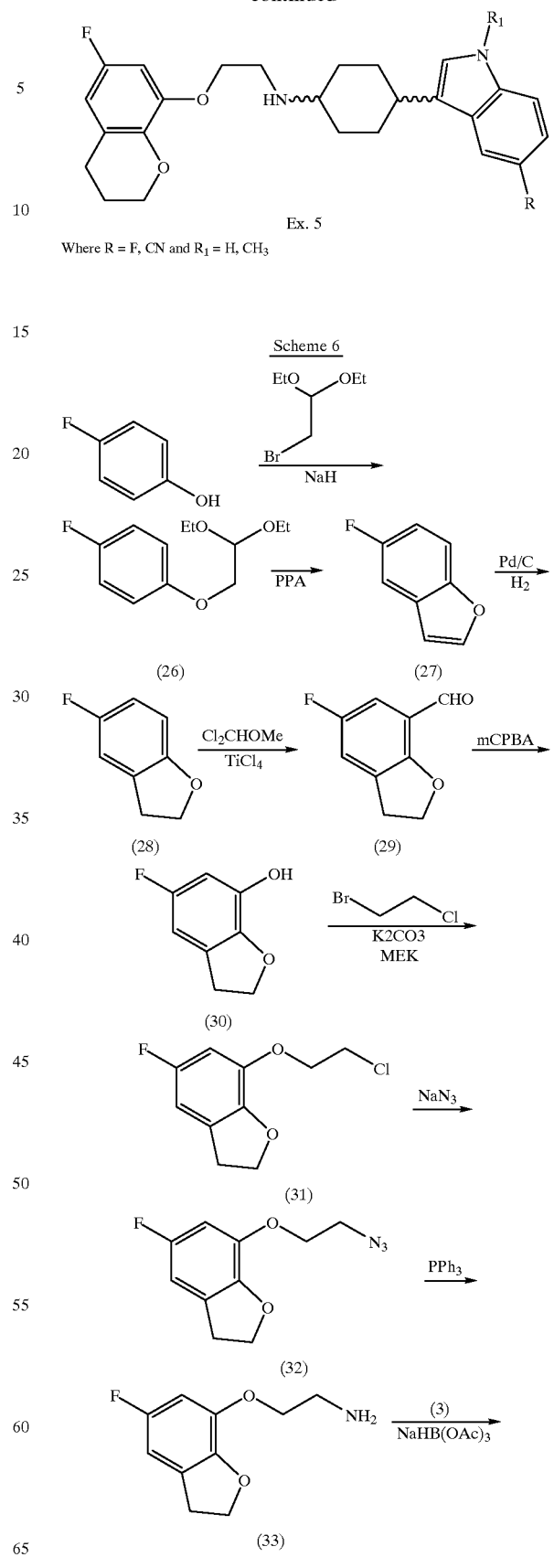

11
-continued
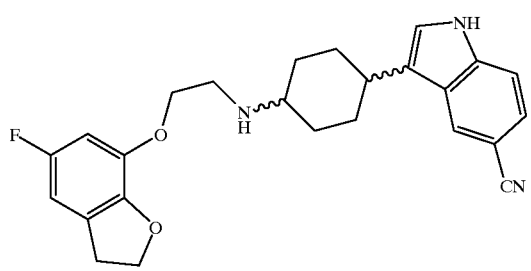
Ex. 6
Scheme 7
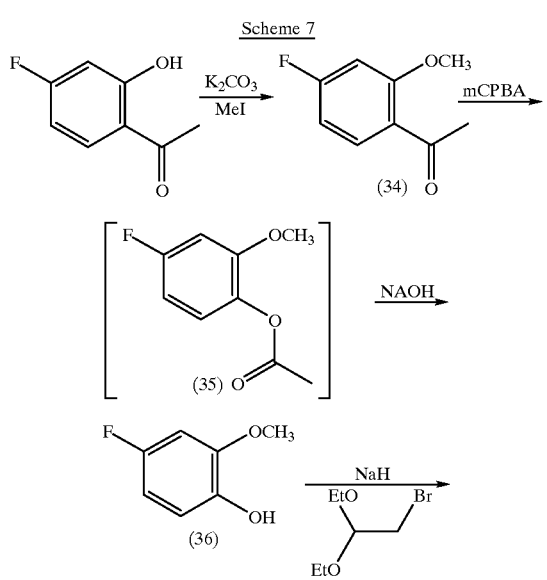
12
-continued
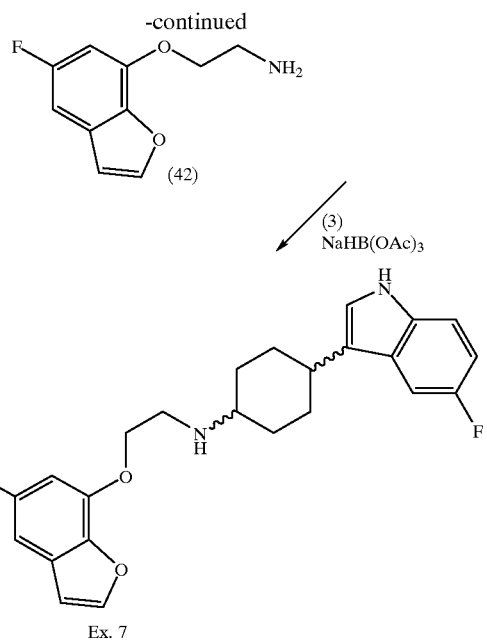
Ex. 7
Scheme 8

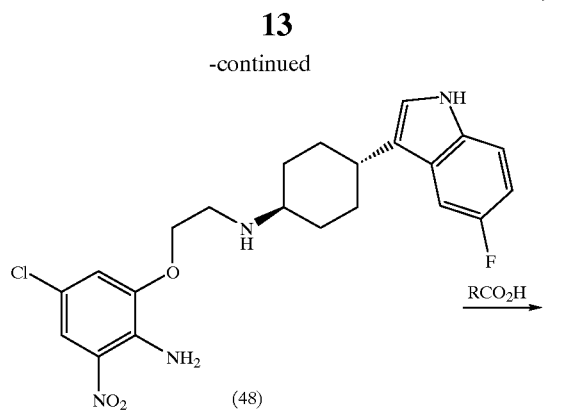
(48)
RCO₂H →
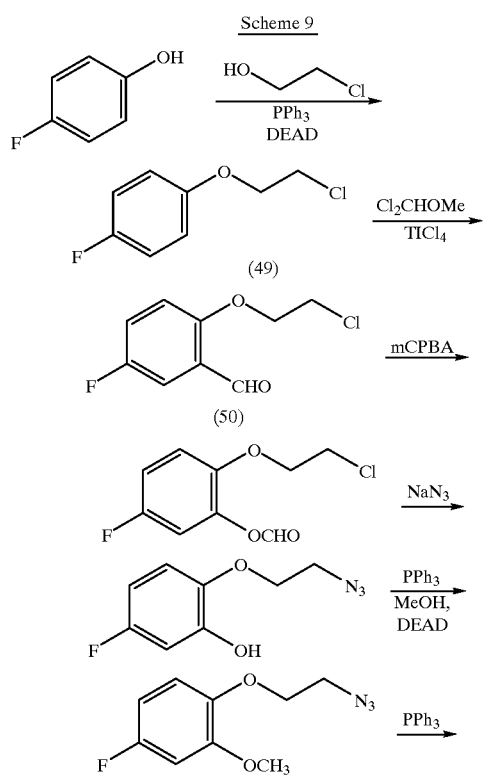
Ex. 8
Scheme 9
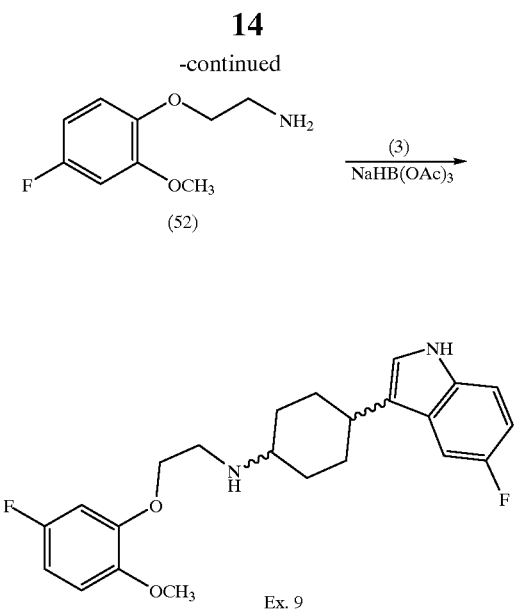
(52)
(3) / NaHB(OAc)₃ →
Ex. 9
Scheme 10
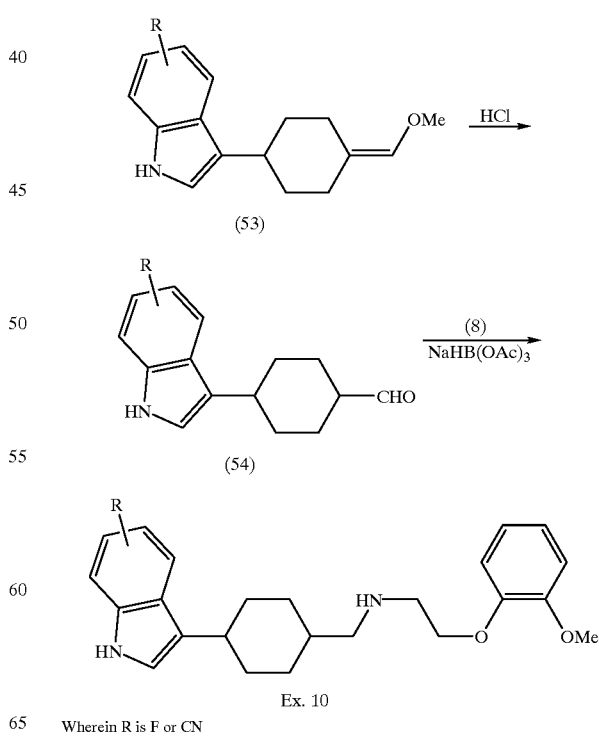
Wherein R is F or CN

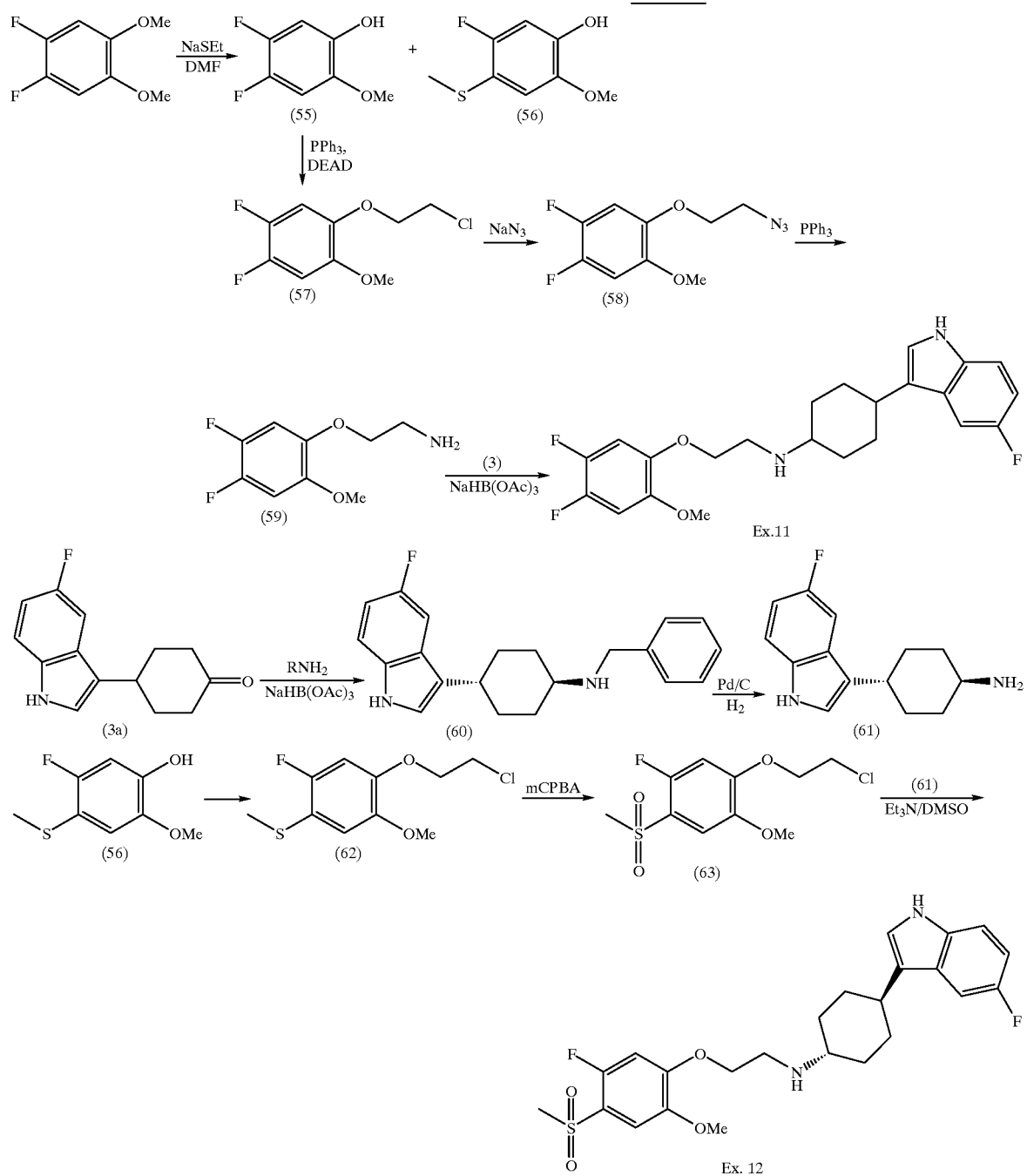
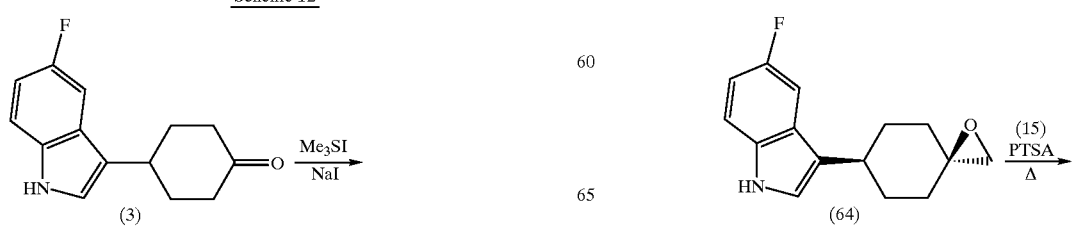

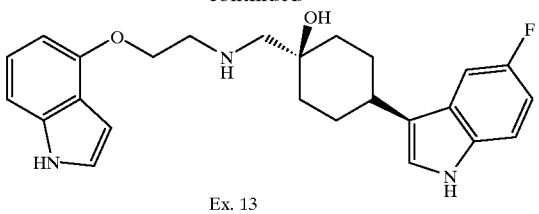

Ex. 13

The present invention will now be illustrated reference to the following, non-limiting examples:

INTERMEDIATE 1

4-(5-Fluoro-1H-3-indolyl)-cyclohex-3-en-ethylene ketal (1a)

5-Fluoroindole (4.96, 0.036 mol), 1,4-cyclohexanedione monoethylene ketal (7.17 g, 0.046 mol) and potassium hydroxide (6 g, 0.043 mol) were heated to reflux in 70 ml methanol for 6 hours. The reaction was cooled and the product was isolated by filtration and washed with water to give 8.59 g (86%) of product as a white solid: mp 153–155° C.

4-(6-Fluoro-1H-3-indolyl)-cyclohex-3-en-ethylene ketal (1b)

This compound was prepared in the manner as described above for (1a) by replacing 5-fluoroindole with 6-fluoroindole (5.14 g, 38 mmol) and obtained in 96.3% yield (10 g) as a white solid: mp 196–197° C.

Elemental analysis for $C_{16}H_{16}FNO_2$ Calc'd: C, 70.32; H, 5.90; N, 5.13 Found: C, 70.62; H, 5.91; N, 5.08

4-(5-Cyano-1H-3-indolyl)-cyclohex-3-en-ethylene ketal (1d)

This compound was prepared in the manner as described above for (1a) by replacing 5-fluoroindole with 5-cyanoindole (29.98 g, 0.21 mol), and obtained in 50% yield (29.32 g) as a white solid: mp 158–160° C.

4-(1H-3-Indolyl)-cyclohex-3-en-ethylene ketal (1d)

Indole (4.69, 40 mmol), 1,4-cyclohexanedione monoethylene ketal (6.3 g, 40 mmol) and potassium hydroxide (13.2 g, 60 mmol) were heated to reflux in 70 ml methanol for 6 hours. The reaction was cooled and the product was isolated by filtration and washed with water to give 9.1 g (89%) of product: MS m/e (M+).

INTERMEDIATE 2

4-(5-Fluoro-1H-3-indolyl)-cyclohexanone ethylene ketal (2a)

A mixture of 4-(5-fluoro-1H-3-indolyl)-cyclohex-3-en-ethylene ketal (8.5 g) and 10% palladium on carbon (2.72 g) in ethanol (200 ml) was hydrogenated for 5 hours. The catalyst was filtered off and the solvent removed under vacuum. Chromatography (methanol-methylene chloride) afforded 7.55 g (82%) of product as a white solid: mp 183–185° C.

4-(6-Fluoro-1H-3-indolyl)-cyclohexanone ethylene ketal (2b)

This compound was prepared in the manner as described above for (2a) by replacing 4-(5-fluoro-1H-3-indolyl)-cyclohex-3-en-ethylene ketal with 4-(6-fluoro-1H-3-indolyl)-cyclohex-3-en-isomer ethylene ketal (9.54 g) in 60% yield (5.83 g) as a white solid: mp 158–159° C.

Elemental analysis for $C_{16}H_{18}FNO_2$ Calc'd: C, 69.80; H, 6.59; N, 5.09 found: C, 69.74; H, 6.48; N, 5.13

4-(5-Cyano-1H-3-indolyl)-cyclohexanone ethylene ketal (2c)

This compound was prepared in the manner as described above for (2a) by replacing 4-(5-fluoro-1H-3-indolyl)-cyclohex-3-en-isomer ethylene ketal with 4-(5-cyano-1H-3-indolyl)-cyclohex-3-en-ethylene ketal (54.6 g) in 95% (52.12 g) yield as a white solid: mp 153–155° C.

4-(1H-3-Indolyl)-cyclohexanone ethylene ketal (2d)

A mixture of 4-(1H-3-indolyl)-cyclohex-3-en-ethylene ketal (8.0 g, 31.3 mmol) and 10% palladium on carbon (1.3 g) in ethanol (700 ml) was hydrogenated overnight. The catalyst was filtered off and the solvent removed under vacuum to afford 8.01 g (99%) of product as a white solid: MS m/e (M+).

INTERMEDIATE 3

4-(5-Fluoro-1H-3-indolyl)-cyclohexanone (3a)

A solution of 4-(5-fluoro-1H-3-indolyl)-cyclohexanone ethylene ketal (2.8 g, 10 mmol) in 2 L (1:1) tetrahydrofuran-hydrochloric acid (1N) was allowed to stir at room temperature for 16 hours. The solvent was evaporated under vacuum. The crude product was dissolved in ethyl acetate, and washed with 1N sodium hydroxide (3×150 ml). The organic layer was dried over anhydrous sodium sulfate and filtered. Chromatography (40% ethyl acetate-hexanes) afforded 2.1 g (91%) of product as yellow solid: mp 112–114° C.

4-(6-Fluoro-1H-3-indolyl)-cyclohexanone (3b)

This compound was prepared in the manner as described above for (3a) by replacing 4-(5-fluoro-1H-3-indolyl)-cyclohexanone ethylene ketal with 4-(6-fluoro-1H-3-indolyl)-cyclohexanone ethylene ketal (5.4 g) in 99% (19.3 g) yield as a white solid: mp 102–105° C.

Elemental analysis for $C_{14}H_{14}NOF$ Calc'd: C, 72.71; H, 6.10; N, 6.06 Found: C, 72.77; H, 5.98; N, 5.96

4-(5-Cyano-1H-3-indolyl)-cyclohexanone (3c)

This compound was prepared in the manner as described above for (3a) by replacing 4-(5-fluoro-1H-3-indolyl)-cyclohexanone ethylene ketal with 4-(5-cyano-1H-3-indolyl)-cyclohexanone ethylene ketal (6 g) in 81% (4.0 g) of product as a white solid: mp 162.5–164° C.

Elemental analysis for $C_{15}H_{14}N_2O$ Calc'd: C, 75.61; H, 5.92; N, 11.76 Found: C, 75.82; H, 6.06; N, 11.72

4-(1H-3-Indolyl)-cyclohexanone (3d)

A solution of 4-(1H-3-indolyl)-cyclohexanone ethylene ketal (2.57 g, 10 mmol) in 200 ml (1:1) tetrahydrofuran-hydrochloric acid (1N) was allowed to stir at room temperature for 16 hours. The solvent was evaporated under vacuum. The crude product was dissolved in ethyl acetate, and washed with 1N sodium hydroxide (3×150 ml). The organic layer was dried over anhydrous sodium sulfate and filtered. Chromatography (40% ethyl acetate-hexanes) afforded 1.9 g (89%) of product.

INTERMEDIATE 4

4-(5-Cyano-1-methyl-3-indolyl)-cyclohex-3-en-ethylene ketal

To a suspension of sodium hydride (60%, 1.74, 0.073 mol) in anhydrous N,N-dimethylformamide (100 ml) was added 4-(5-cyano-1H-3-indolyl)-cyclohex-3-en-isomer ethylene ketal (9.9 g, 0.035 mol) at room temperature. The mixture was stirred for 30 minutes at room temperature, then methyl iodide (9 ml, 0.14 mol) was added at room temperature. The reaction was allowed to stir for 1 hour, then was quenched with water (50 ml). The mixture was extracted with methylene chloride (3×150 ml) and water (3×150 ml). The organic layer was dried over magnesium sulfate and filtered. The solvent was removed under vacuum. Chromatography (5% methanol-methylene chloride) afforded 2.54 g of product as a light yellow solid: mp 65–67° C.

Elemental analysis for $C_{18}H_{18}N_2O_2$ Calc'd: C, 73.45; H, 6.16; N, 9.52 Found: C, 73.17; H, 6.24; N, 9.43

INTERMEDIATE 5

4-(5-Cyano-1-methyl-3-indolyl)cyclohexanone ethylene ketal

A mixture of 4-(5-cyano-1-methyl-3-indolyl)-cyclohex-3-en-isomer ethylene ketal (3.77 g) and 10% palladium on carbon (0.99 g) in ethanol-tetrahydrofuran (200:80 ml) was hydrogenated for 5 hours. The catalyst was filtered off and the solvent was removed under vacuum to afford a white powder which was washed with ethanol-hexanes (1:1) and dried under vacuum for 4 hours (2.75 g): mp 170–172° C.

Elemental analysis for $C_{18}H_{20}N_2O_2$ Calc'd: C, 72.95; H, 6.80; N, 9.45 Found: C, 72.79; H, 6.82; N, 9.35

INTERMEDIATE 6

4-(5-Cyano-1-methyl-3-indolyl)cyclohexanone

A solution of 4-(5-cyano-1-methyl-3-indolyl)-cyclohexanone ethylene ketal (5.5 g) in 150 ml (1:1) tetrahydrofuran-hydrochloric acid (1N) was allowed to stir at room temperature for 16 hours, then to above solution sodium bicarbonate (4.49 g) was added. The mixture was extracted with methylene chloride (3×100 ml) and washed with brine (3×150 ml). The organic layer was dried over anhydrous magnesium sulfate and filtered. The solvent was removed to afford a light brown solid which was boiled in ethyl acetate-hexanes (1:1). The mixture was cooled to room temperature and solid was collected and dried under vacuum (2.06 g): mp 150–152° C.

Elemental analysis for $C_{15}H_{15}N_2O$ Calc'd: C, 76.16; H, 6.39; N, 11.10 Found: C, 75.84; H, 6.34; N, 10.92

INTERMEDIATE 7

2-(2-Methoxy-phenoxy)acetonitrile

To a suspension of sodium hydride (2.4 g, 60 mmol) in N,N-dimethylformamide (100 ml) was added guaiacol (6.3 g, 50 mmol) at room temperature. The mixture was allowed to stir for 40 minutes at room temperature. To above reaction mixture was added bromoacetonitrile (7 ml, 100 mmol). The reaction mixture was stirred for 3 hours and then quenched with water. The mixture was extracted with ethyl ether (3×150 ml), washed with water (3×150 ml) and brine (3×100 ml). The organic layer was dried over anhydrous sodium sulfate and filtered. Chromatography (20% ethyl acetate-hexanes) afforded 7.0 g (86%) of product as a clear oil: MS m/e (M+).

INTERMEDIATE 8

2-(2-Methoxy-phenoxy)ethylamine

To a solution of 2-(2-methoxy-phenoxy)acetonitrile (5 g, 31 mmol) in anhydrous ethyl ether (100 ml) was added lithium aluminum hydride (1.6 g, 40 mmol) portionwise. The reaction mixture was heated to reflux for 3 hours and then cooled to 0° C. The reaction was quenched with 1N hydrochloric acid and diluted with water (PH=1, aqueous layer). The mixture was extracted with ethyl acetate (3×150 ml), neutralized with 50% sodium hydroxide to pH>10, and extracted again with more ethyl acetate (3×100 ml). The combined organic layers were washed with brine (3×150 ml), dried over anhydrous sodium sulfate and filtered. The solvent was removed under vacuum to afford 2.85 g (56%) of product as an oil; MS EI m/e 167 (M$^+$).

INTERMEDIATE 11

2-(5-Fluoro-2-methoxy-phenoxy)ethylchloride

A solution of 5-fluoro-2-methoxy phenol (4.34 g, 31 mmol) prepared according to the procedure set forth in Mancini et al., Synth. Comm., 19:2001 (1989), 1-bromo-2-chloroethane (8.9 ml, 107 mmol) and potassium carbonate (14.8 g, 106 mmol) in 2-butanone (60 ml) was refluxed for 24 hours. The mixture was poured into water (150 ml), extracted with methylene chloride (3×150 ml) and washed with brine (3×100 ml). The organic layer was dried over anhydrous sodium sulfate, filtered and the solvent was removed under vacuum. Chromatography (20% ethyl acetate-hexanes) afforded 4.8 g (76%) of product as a clear oil.

Elemental analysis for $C_9H_{10}FClO_2$ Calc'd: C, 52.83; H, 4.93 Found: C, 52.79; H, 4.75

INTERMEDIATE 12

2-(5-Fluoro-2-methoxy-phenoxy)ethylazide

A solution of 2-(5-fluoro-2-methoxy-phenoxy)ethylchloride (4.0 g, 19 mmol) and sodium azide (2.6 g, 39 mmol) in anhydrous N,N-dimethylformamide (60 ml) was allowed to stir at 60° C. for 18 hours. The mixture was poured into water (150 ml), extracted with methylene chloride (3×150 ml) and washed with water (3×100 ml). The organic layer was dried over anhydrous sodium sulfate, filtered and the solvent was removed under vacuum. Chromatography (20% ethyl acetate-hexanes) afforded 3.8 g (92%) of product as a clear oil.

Elemental analysis for $C_9H_{10}FN_3O_2$ Calc'd: C, 51.18; H, 4.77; N, 19.90 Found: C, 51.35; H, 4.71; N, 20.06

INTERMEDIATE 13

2-(5-Fluoro-2-methoxy-phenoxy)ethylamine

A solution of 2-(5-fluoro-2-methoxy-phenoxy)ethylazide (3.97 g, 0.019 mol) and triphenylphosphine (5.95 g, 0.023 mol) in tetrahydrofuran (80 ml) and water (1.5 ml) was allowed to stir for 18 hours at room temperature. The solvent was removed under vacuum. Chromatography (ethyl acetate followed by 25–50% methanol-ethyl acetate plus ammonium hydroxide) removed triphenylphosphine and triphenylphosphine oxide and afforded 3.14 g (90%) of product as a clear oil. MS EI m/e 185 (M$^+$)

INTERMEDIATE 14

2-(1H-Indol-4-yloxy)acetonitrile

To a solution of 4-hydroxyindole (3 g, 22.5 mmol) in anhydrous N,N-dimethylformamide (20 ml) was added sodium hydride (60%, 1.08 g, 27 mmol) at room temperature. After the reaction was allowed to stir for 40 minutes at room temperature, bromoacetonitrile (3.13 ml, 45 mmol) was added thereto. The reaction was allowed to stir overnight at room temperature, was then quenched with water. The mixture was extracted with ethyl acetate (3×100 ml) and washed with brine (3×100 ml). The organic layer was dried over anhydrous sodium sulfate and filtered. The solvent was removed under vacuum. Chromatography (30% ethyl acetate-hexanes) afforded 3.75 g (90%) of product as a oil.

INTERMEDIATE 15

2-(1H-Indol-4-yloxy)ethylamine

To a solution of 2-(1H-indol-4-yloxy)-acetonitrile (0.9 g, 5.2 mmol) in anhydrous ethyl ether (30 ml) was added lithium aluminum hydride (95%, 0.21 g, 5.2 mmol) at room temperature. The reaction was allowed to reflux for 2 hours, another equivalent of lithium aluminum hydride (0.21 g, 5.2 mmol) was added. The reaction was allowed to reflux for another 2 hours and then was quenched with 1N sodium hydroxide and water. The solid was removed by filtration and the filtrate was concentrated and dissolved in methanol and water. To a above mixture was added 2N hydrochloric acid until pH<3 and then extracted with ethyl ether. To the above aqueous layer was added sodium hydroxide until pH>9, the mixture was extracted with isopropanol-methylene (1:3). The combined organic layers were washed with brine, and dried over anhydrous sodium sulfate. The solvent was removed under vacuum to afford 0.3 g (33%) of product as a brown solid. mp: 123–125° C.; MS EI m/e 177 ($M^+$)

INTERMEDIATE 16

5-Hydroxy-(2,3)-dihydrobenzo[1,4]dioxin

Pyrogallol (5 g, 0.04 mol) was dissolved in 2-butanone (600 ml) and potassium carbonate (1.82 g, 0.013 mol) was added to the resulting product. The mixture was stirred at reflux while 1,2-dibromoethane (2.48 g, 1.14 ml, 0.013 mol) was slowly added dropwise. The reaction was allowed to stir overnight and then was cooled to room temperature. The mixture was poured into water (100 ml) and extracted with methylene chloride (200 ml). The organic layer was dried over anhydrous sodium sulfate, filtered, and the solvent was removed under vacuum. Chromatography (5% methanol-methylene chloride) afforded 2.74 g (45%) of product as a clear oil; MS EI m/e 152 ($M^+$).

INTERMEDIATE 17

5-(2-Chloroethoxy)-(2,3)-dihydrobenzo[1,4]dioxin

To solution of 5-hydroxybenzodioxin (1.0 g, 6.5 mmol) and 2-chloroethanol (0.79 g, 9.9 mmol), triphenylphosphine (2.6 g, 9.9 nmol) in tetrahydrofuran (50 ml) was slowly added diisopropyl azodicarboxylate (DIAD) (2.0 g, 9.8 mmol). After 2 hours, another 1.5 eq of triphenylphosphine, DIAD, and 2-chloroethanol was added and the reaction stirred for another 2 hours. The reaction mixture was poured into water (100 ml), and extracted with methylene chloride (100 ml). The organic layer was separated and dried over anhydrous magnesium sulfate, filtered, and the solvent removed under vacuum. Chromatography (20% ethyl acetate-hexanes) afforded 1.7 g (76%) of product as a white solid: mp 70.5–72.5° C.

Elemental analysis for $C_{10}H_{11}ClO_3$ Calc'd C, 55.96; H, 5.17 Found: C, 55.57; H, 5.20

INTERMEDIATE 18

2-(2,3-Dihydrobenzo[1,4]dioxin-5-yloxy)ethylazide

A solution of 5-(2-chloroethoxy)-(2,3)-dihydrobenzo[1,4] dioxin (4.6 g, 0.02 mol) and sodium azide (2.78 g, 0.043 mol) in anhydrous N,N-dimethyl-formamide (100 ml) was allowed to stir for 18 hours at 60° C. The mixture was poured into water (200 ml) and extracted with methylene chloride (3×100 ml). The organic layer was washed with water (3×150 ml), dried over anhydrous sodium sulfate, filtered, and the solvent removed under vacuum. Chromatography (20% ethyl acetate-hexanes) afforded 3.43 g (72%) of product as a clear oil. MS FAB m/e 221 ($M^+$)

INTERMEDIATE 19

2-(2,3-Dihydrobenzo[1,4]dioxin-5-yloxy)ethylamine

A solution of 2-(2,3-dihydrobenzo[1,4]dioxin-5-yloxy) ethylazide (3.43 g, 0.016 mol) and triphenylphosphine (6.3 g, 0.023 mol) in tetrahydrofuran (50 ml) and water (2 ml) was allowed to stir for 18 hours at room temperature. The solvent was removed under vacuum. Chromatography (30% methanol-methylene chloride plus ammonium hydroxide) afford 1.93 g (62%) of product as a yellow oil: MS FAB m/e 196 $(M+H)^+$

INTERMEDIATE 20

6-Fluorochroman

A mixture of 6-fluoro-4-oxo-chroman (2 g, 12 mmol) and 10% palladium on carbon (1 g) in concentrated hydrochloric acid (20 ml) and ethanol (30 ml) was hydrogenated for 20 hours. The catalyst was filtered and the solvent removed under vacuum. The residue was dissolved in ethyl acetate (100 ml), washed with 1N NaOH (6×200 ml) and water (3×150 ml), dried over anhydrous sodium sulfate, filtered and the solvent was removed under vacuum. Chromatography (20% ethyl acetate-hexanes) afforded 1.41 g (77%) of product as a clear oil: MS EI m/e 152 ($M^+$).

INTERMEDIATE 21

6-Fluorochroman-8-carbaldehyde

To a solution of 6-fluorochroman (0.7 g, 4.6 mmol) in anhydrous methylene chloride (20 ml) was slowly added $TiCl_4$ (1.57 g, 8.3 mmol) and α,α'-dichloromethyl methyl ether (0.53 g, 4.6 mmol) at 0° C. The reaction was allowed to reach room temperature slowly and was stirred for 16 hours. The reaction mixture was poured into ice-water, extracted with methylene chloride (3×100 ml), washed with saturated sodium carbonate (5×150 ml) and brine (3×100 ml). The organic layer was dried over anhydrous sodium sulfate, filtered, and the solvent was removed under vacuum. The crude solid was collected and dried under the vacuum to afford 0.75 g (90%) of product as a yellow solid: mp 55–57° C.

Elemental analysis for $C_{10}H_9FO_2$ Calc'd: C, 66.66; H, 5.04 Found: C, 66.64; H, 4.78

INTERMEDIATE 22

6-Fluoro-8-hydroxychroman

To a solution of 6-fluorochroman-8-carbaldehyde (8.6 g, 48 mmol), 3-t-butyl-4-hydroxy-5-methylphenyl sulfide (100 mg) in anhydrous methylene chloride (60 ml) at 0° C. was added 3-chloroperoxybenzoic acid (mCPBA) (12.4 g, 70 mmol) portionwise. The reaction mixture was allowed to reflux for 16 hours. The excess mCBPA was destroyed by adding 10% sodium sulfite. The benzoic acid was filtered, and the filtrate was extracted with methylene chloride (3×150 ml), and washed with water (3×150 ml). The organic layer was dried over anhydrous sodium sulfate and filtered. The solvent was removed under vacuum and crude product (10.2 g, 52 mmol) was dissolved in ethanol-water (200 ml, 1:1). Sodium hydroxide (6.2 g, 160 mmol) was added to above solution at 0° C. After 30 minutes the ice bath was removed, and the reaction mixture was allowed to stir for 3 hours at room temperature. Ethanol was evaporated,. The residue was neutralized with concentrated hydrochloric acid, extracted with methylene chloride (3×150 ml) and washed with saturated sodium bicarbonate (2×100 ml) and brine (2×100 ml). The organic layer was dried over sodium sulfate, filtered and the solvent was removed under vacuum. Chromatography (25% ethyl acetate-hexanes) afforded 6.9 g (79%) of product as a white solid: mp 62–63° C.

Elemental analysis for $C_9H_9FO_2$ Calc'd: C, 64.28; H, 5.39 Found: C, 64.31; H, 5.27

INTERMEDIATE 23

2-(6-Fluorochroman-8-yloxy)ethylchloride

A solution of 6-fluorochroman-8-carbaldehyde (5.5 g, 33 mmol), 1-bromo-2-chloroethane (16.4 g, 114 mmol) and potassium carbonate (16 g, 114 mmol) in 2-butanone (60 ml) was refluxed for 24 hours. The mixture was poured into water (150 ml), extracted with methylene chloride (3×150 ml) and washed with brine (3×100 ml). The organic layer was dried over sodium sulfate, filtered and the solvent was removed under vacuum. Chromatography (20% ethyl acetate-hexanes) afforded 5.74 g of product as a white solid: mp 89–90° C.

Elemental analysis for $C_{11}H_{12}FClO_2$ Calc'd: C, 57.28; H, 5.24 Found: C, 57.15; H, 5.69

INTERMEDIATE 24

2-(6-Fluorochroman-8-yloxy)ethylazide

A solution of 2-(6-fluorochroman-8-yloxy)ethylchloride (4.13 g, 0.018 mol) and sodium azide (2.33 g, 0.036 mol) in anhydrous N,N-dimethylformamide (60 ml) was allowed to stir at 60° C. for 18 hours. The mixture was poured into water (150 ml), extracted with methylene chloride (3×150 ml) and washed with water (3×100 ml). The organic layer was dried over sodium sulfate, filtered and the solvent was removed under vacuum. Chromatography (20% ethyl acetate-hexanes) afforded 4.12 g (97%) of product as a clear oil.

Elemental analysis for $C_{11}H_{12}FN_3O_2$ Calc'd: C, 55.69; H, 5.10; N, 17.71 Found: C, 55.44; H, 4.97; N, 17.88

INTERMEDIATE 25

2-(6-Fluorochroman-8-yloxy)ethylamine

A solution of 2-(6-fluorochroman-8-yloxy)ethylazide (4.12 g, 0.017 mol) and triphenylphosphine (6.83 g, 0.026 mol) in tetrahydrofuran (80 ml) and water (1.5 ml) was allowed to stir for 18 hours at room temperature. The solvent was removed under vacuum. Chromatography (ethyl acetate) removed triphenylphosphine and triphenylphosphine oxide (40% methanol-methylene chloride plus ammonium hydroxide) to afford 3.45 g (94%) of product as a white solid: mp 68–70° C.

Elemental analysis for $C_{11}H_{14}FNO_2$ Calc'd: C, 62.55; H, 6.68; N, 6.63 Found: C, 62.18; H, 6.54; N, 6.63

INTERMEDIATE 26

2-(4-Fluorophenoxy)-acetaldehyde Diethyl Acetal

To a suspension of sodium hydride (5.4 g, 0.134 mol) in anhydrous N,N-dimethylformamide (100 ml) was added 4-fluorophenol (10 g, 0.089 mol) at 0° C. After hydrogen evolution had ceased, bromo-acetaldehyde diethyl acetal (16 ml, 0.11 mol) was added. The reaction was heated at 160–170° C. for 18 hours. The mixture was poured into ice-water, extracted with ethyl acetate (3×150 ml) and washed with 1N sodium hydroxide (3×100 ml) and brine (3×100 ml). The organic layer was dried over anhydrous sodium sulfate, filtered, and the solvent was removed under vacuum. Chromatography (25% ethyl acetate-hexanes) afforded 16.36 g (80%) of product as a clear oil: MS EI m/e 228 ($M^+$).

INTERMEDIATE 27

5-Fluorobenzofuran

To a mixture of benzene (200 ml) containing polyphosphoric acid (7.9 g, 0.035 mol) was added 2-(4-fluorophenoxy)-acetaldehyde diethyl acetal (8 g, 0.035 mol). The mixture was stirred vigorously while being heated to reflux for 2.5 hours. The reaction mixture was cooled to room temperature and decanted from the polyphosphoric acid. The solvent was removed under vacuum. Chromatography (5% ethyl acetate-hexanes) afforded 3.4 g (45%) of product as a clear oil: $^1$H NMR ($CDCl_3$ or DMSO-$d_6$) δ6.74 (dd, 1H, J=2.0, 0.6 Hz), 7.01 (td, 1H, J=9, 2.7 Hz), 7.25 (dd, 1H, J=8.4, 2.7 Hz), 7.43 (dd, 1H, J=9, 3.9 Hz), 7.65 (d, 1H, J=1.8 Hz).

INTERMEDIATE 28

5-Fluoro-2,3-dihydrobenzofuran

A solution of 5-fluorobenzofuran and 10% palladium on carbon in acetic acid (25 ml) was hydrogenated under 50 psi for 12 hours. The catalyst was filtered through celite and the celite was washed with methylene chloride (200 ml). The organic layer was washed with 1N NaOH (3×100 ml) and brine (3×100 ml) and dried over anhydrous sodium sulfate and filtered. The solvent was removed under vacuum to afforded 2.59 g (85%) of product as a clear oil: $^1$H NMR (300 MHz, $CDCl_3$): δ3.12 ppm (t, 2H, J=8.7 Hz), 4.58 (t, 2H, J=8.7 Hz), 6.68 (dd, 1H, J=8.7, 4.2 Hz), 6.79 (tm, 1H, J=8.7 Hz), 6.89 (dm, 1H, J=8.1 Hz).

INTERMEDIATE 29

5-Fluoro-2,3-dihydrobenzofuran-7-carbaldehyde

To a solution of 5-fluoro-2,3-dihydrobenzofuran (7 g, 0.051 mol) in anhydrous methylene chloride (40 ml) was added titanium (IV) chloride (9.5 ml, 0.087 mol) followed by α,α'-dichloromethyl methyl ether (4.6 ml, 0.051 mol) at 0° C. The reaction was allowed to reach room temperature slowly and stirred overnight. The reaction mixture was poured into ice-water slowly, extracted with methylene chloride (3×100 ml) and washed with saturated sodium carbonate (5×100 ml) and brine (3×100 ml). The organic layer was dried over anhydrous sodium sulfate and filtered. Chromatography (25% ethyl acetate-hexanes) afforded 3.29 g (39%) of product as a white solid: mp 103–104° C.

Elemental analysis for $C_9H_7FO_2$ Calc'd: C, 65.06; H, 4.75 Found: C, 65.01; H, 4.03

INTERMEDIATE 30

5-Fluoro-7-hydroxy-2,3-dihydro-benzofuran

To a solution of 5-fluoro-2,3-dihydrobenzofuran-7-carbaldehyde (3.29 g, 20 mmol), 3-t-butyl-4-hydroxy-5-methylphenyl sulfide (100 mg) in anhydrous methylene chloride (40 ml) at 0° C. was added 3-chloroperoxybenzoic acid (mCPBA) (8.5 g, 30 mmol) portionwise. The reaction mixture was refluxed for 16 hours. The excess mCPBA was destroyed by adding 10% sodium sulfite. The benzoic acid was filtered off, and the filtrate was extracted with methylene chloride (3×100 ml) and washed with water (3×100 ml). The organic layer was dried over anhydrous sodium sulfate and filtered. The solvent was removed under vacuum and the crude product was dissolved in ethanol-water (100 ml, 1:1). To the above solution was added sodium hydroxide (2.11 g, 53 mmol) at 0° C. After 30 minutes the ice bath was removed, and the reaction mixture was allowed to stir for 3 hours at room temperature. The ethanol was evaporated and the residue was neutralized with concentrated hydrochloric acid, extracted with methylene chloride (3×100 ml) and washed sequentially with saturated sodium bicarbonate (2×100 ml) and brine (2×100 ml). The organic layer was dried over sodium sulfate, filtered and the solvent was removed under vacuum. Chromatography (30% ethyl acetate-hexanes) afforded 1.62 g (50%) of product as a white solid: mp 102.5–103.5° C.

Elemental analysis for $C_8H_7FO_2$ Calc'd: C, 62.34; H, 4.58 Found: C, 62.19; H, 4.59

INTERMEDIATE 31

2-(5-Fluoro-2,3-dihydro-benzofuran-7-yloxy) ethylchloride

A solution of 5-fluoro-7-hydroxy-2,3-dihydro-benzofuran (1.6 g, 10 mmol), 1-bromo-2-chloroethane (7.8 g, 55 mmol) and potassium carbonate (2.2 g, 16 mmol) in 2-butanone (40 ml) was refluxed for 24 hours. The mixture was poured into water (150 ml), extracted with methylene chloride (3×150 ml) and washed with brine (3×100 ml). The organic layer was dried over anhydrous sodium sulfate, filtered and the solvent was removed under vacuum. Chromatography (25% ethyl acetate-hexanes) afforded 2.10 g of product as a white solid: mp 72.5–74.5° C.

Elemental analysis for $C_{10}H_{10}FClO_2$ Calc'd: C, 55.44; H, 4.65 Found: C, 55.37; H, 4.58

INTERMEDIATE 32

2-(5-Fluoro-2,3-dihydrobenzofuran-7-yloxy) ethylazide

A solution of 2-(5-fluoro-2,3-dihydro-benzofuran-7-yloxy)ethylchloride (2.05 g, 9.4 mmol) and sodium azide (1.23 g, 19 mol) in anhydrous N,N-dimethylformide (30 ml) was allowed to stir at 60° C. for 24 hours. The mixture was poured into water (100 ml), extracted with methylene chloride (3×150 ml) and washed with water (3×100 ml). The organic layer was dried over sodium sulfate, filtered and the solvent was removed under vacuum. Chromatography (20% ethyl acetate-hexanes) afforded 2.0 g (95%) of product as a clear oil: MS ESI m/e 241 [M+1]$^+$.

INTERMEDIATE 33

2-(5-Fluoro-2,3-dihydrofuran-7-yloxy)ethylamine

A solution of 2-(5-fluoro-2,3-dihydrobenzofuran-7-yloxy)ethylazide (1.98 g, 89 mmol) and triphenylphosphine (2.8 g, 10.6 mmol) in tetrahydrofuran (50 ml) and water (1.5 ml) was allowed to stir for 18 hours at room temperature. The solvent was removed under vacuum. Chromatography (ethyl acetate) removed triphenylphosphine and triphenylphosphine oxide and (40% methanol-methylene chloride plus ammonium hydroxide) afforded 2.0 g (100%) of product as a clear oil: MS ESI m/e 198 [M+1]$^+$

INTERMEDIATE 34

4-Fluoro-2-methoxyacetophenone

A solution of 4-fluoro-2-hydroxyacetophenone (1 g, 6.5 mmol), methyl iodide (0.4 ml), potassium carbonate (1.34 g, 9.7 mmol) in anhydrous dimethylsulfoxide (20 ml) was allowed to stir at room temperature for 2 hours. The mixture was poured into water (100 ml) and extracted with methylene chloride (3×100 ml). The organic layer was dried over anhydrous sodium sulfate and filtered. The solvent was removed under vacuum to afford 1.1 g (100%) of product as a light yellow solid: mp 50–51.5° C.

Elemental analysis for $C_9H_9FO_2$ Calc'd: C, 64.28; H, 5.39 Found: C, 64.22; H, 5.49

INTERMEDIATE 36

4-Fluoro-2-methoxyphenol

To a cooled (0° C.) solution of 4-fluoro-2-methoxyacetophenone (16.8 g, 0.1 mol) and 3-tert-butyl-4-hydroxy-5-methylphenyl sulfide (200 mg) in methylene chloride (300 ml) was added 3-chloroperoxybenzoic acid (m-CPBA) (37 g, 0.15 mol) portionwise over a period of 5 minutes under an inert atmosphere. The mixture was refluxed for 14 hours. The solution was cooled to 0° C., and the excess m-CPBA was destroyed by vigorously stirring with 10% aqueous sodium sulfite for 20 minutes. The organic layer was separated and then washed with equal volumes of water (3×150 ml), 5% sodium bicarbonate, water and brine. The organic layer was dried over anhydrous sodium sulfate, filtered and the solvent was removed under vacuum affording a yellow oil. The yellow oil was dissolved in 200 ml ethanol-water (1:1) and sodium hydroxide (0.3 mol) was added at 0° C. under inert atmosphere. After 0.5 hour the ice-bath was removed and the reaction mixture stirred at room temperature for 2 hours. Evaporation of the solvent under vacuum followed by neutralization with concentrated hydrochloric acid precipitated an oil which was extracted with methylene chloride (150 ml). The organic layer was washed with equal volumes of water (3×150 ml) and brine. The organic layer was dried over anhydrous sodium sulfate and filtered. The solvent was removed under vacuum. Chromatography (25% ethyl acetate-hexanes) afforded 10.0 g (71%) of product as a light-yellow oil; MS EI m/e 142 (M$^+$).

INTERMEDIATE 37

2-(2-Methoxy-4-fluorophenoxy)-acetaldehyde Diethyl Acetal

To a suspension of sodium hydride (5.4 g, 0.13 mol) in anhydrous N,N-dimethyl-formamide (100 ml) was added 4-fluoro-2-methoxyphenol (12.05 g, 0.085 mol) at 0° C. After $H_2$ evolution had ceased, bromo-acetaldehyde diethyl acetal (14.66 ml, 0.1 mol) was added. The reaction was heated at 160–170° C. for 18 hours. The mixture was poured into ice-water, extracted with ethyl acetate (3×150 ml) and washed sequentially with 1N sodium hydroxide (3×100 ml)

and brine (3×100 ml). The organic layer was dried over anhydrous sodium sulfate and filtered. The solvent was removed under vacuum. Chromatography (25% ethyl acetate-hexanes) afforded 21.48 g (98%) of product as a yellow oil: MS EI m/e 258 (M+).

INTERMEDIATE 38

5-Fluoro-7-methoxy-benzofuran

To a mixture of xylene (100 ml) containing polyphosphoric acid (40 g) was added 2-(2-methoxy-4-fluoro-phenoxy)-acetaldehyde diethyl acetal (10 g). The mixture was stirred while being heated to reflux for 0.5 hour. The reaction mixture was cooled to room temperature, and decanted from the polyphosphoric acid. The solvent was removed under vacuum. Chromatography (25% ethyl acetate-hexanes) afforded 1.74 g (15%) of product as a yellow oil: MS EI m/e 166 (M+)

INTERMEDIATE 39

5-Fluoro-7-hydroxybezofuran

5-Fluoro-7-methoxybenzofuran (2.16 g, 13 mmol) was dissolved in anhydrous methylene chloride (25 ml) in 100 ml round-bottom flask. The flask was placed in an acetone-ice bath at −78° C. The flask was fitted with a air-condenser. A solution of boron tribromide in methylene chloride (1 M, 19.5 ml) was added carefully to the stirred solution through the condenser. The reaction was kept at −78° C. for 6 hours, then was allowed to stir at room temperature overnight. The reaction was quenched by adding water (20 ml) and diluted with ethyl ether. The solvent was removed under vacuum. Chromatography (25% ethyl acetate-hexanes) afforded 1.4 g (71%) of product as a yellow oil. MS EI 152 m/e (M+)

INTERMEDIATE 40

2-(5-Fluoro-benzofuran-7-yloxy)-ethylchloride

To a solution of 5-fluoro-7-hydroxybenzofuran (1.4 g, 9.2 mmol), triphenylphosphine (6 g, 23 mmol), 2-chloroethanol (1.53 ml, 23 mmol) in tetrahydrofuran (50 ml) was slowly added diisopropyl azodicarboxylate (4.5 ml, 23 mmol). The reaction was stirred at room temperature for 2 hours, and the tetrahydrofuran was removed under vacuum. Chromatography (25% ethyl acetate-hexanes) afforded 1.76 g (89%) of product as a yellow oil: MS EI 214 m/e (M+).

INTERMEDIATE 41

2-(5-Fluoro-benzofuran-7-yloxy)-ethylazide

A solution 2-(5-fluoro-benzofuran-7-yloxy)-ethylchloride (4.6 g, 0.02 mol) and sodium azide (2.78 g, 0.043 mol) in anhydrous N,N-dimethylformamide (100 ml) was allowed to stir for 18 hours at 60° C. The mixture was poured into water (200 ml), and extracted with methylene chloride (3×100 ml). The organic layer was washed with water (3×150 ml), dried over anhydrous sodium sulfate, filtered, and the solvent removed under vacuum. Chromatography (20% ethyl acetate-hexanes) afforded 3.43 g (72%) of product as a clear oil: MS FAB m/e 221 (M+)

INTERMEDIATE 42

2-(5-Fluoro-benzofuran-7-yloxy)-ethylamine

A solution 2-(5-fluoro-benzofuran-7-yloxy)-ethylazide (0.82 g, 3.7 mmol) and triphenylphosphine (1.17 g, 4.4 mmol) in tetrahydrofuran (50 ml) and water (2 ml) was allowed to stir for 18 hours at room temperature. The solvent was removed under vacuum. Chromatography (30% methanol-methylene chloride plus ammonium hydroxide) afford 0.55 g (73%) of product as a yellow oil: MS ESI 196 m/e (M+H)+

INTERMEDIATE 43

2-(2-Chloro-ethoxy)-6-nitro-phenylamine

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 ml) was refluxed for 24 hours. The mixture was cooled, filtered and the solids were washed with ethyl acetate. The filtrate was concentrated to an oily residue that was dissolved in ethyl acetate (500 ml). The organic layer was washed sequentially with 1N sodium hydroxide (250 ml), water (500 ml) and brine (2×500 ml) and then dried over anhydrous magnesium sulfate. Concentration of the filtered solution and trituration of the residue with hexanes afforded 37.8 g (84.6%) of product as an orange solid: mp 71–73° C.; MS EI m/e 216 (M+).

Elemental analysis for $C_8H_9ClN_2O_3$ Calc'd: C, 44.36; H, 4.19; N, 12.93 Found: C, 44.45; H, 4.02; N, 12.97

INTERMEDIATE 44

2-(2-Chloro-ethoxy)-4-chloro-6-nitro-phenylamine

A solution of 2-(2-chloro-ethoxy)-6-nitro-phenylamine (30.0 g, 0.14 mol), N-chlorosuccinimide and acetonitrile (1.3 L) was refluxed for 4 hours. The mixture was concentrated under vacuum and the residue was diluted with ethyl acetate (500 ml). The organic layer was washed with water (2×250 ml) and brine (250 ml), dried over anhydrous magnesium sulfate, filtered, and the solvent removed under vacuum to give an orange solid residue. Crystallization from ethyl acetate-hexanes gave 33.5 g (95.3%) of product as an orange solid: mp 109–110° C.; MS (EI) 250/252/254 m/e (M+).

Elemental analysis for $C_8H_8Cl_2N_2O_3$ Calc'd: C, 38.27; H, 3.21; N, 11.16 Found: C, 38.15; H, 3.10; N, 10.96

INTERMEDIATE 45

2-(2-Azido-ethoxy)-4-chloro-6-nitro-phenylamine

A solution of 2-(2-chloro-ethoxy)-4-chloro-6-nitro-phenylamine (3.07 g, 12.2 mmol), sodium azide (1.59 g, 24.4 mmol) in anhydrous N,N-dimethylformamide (30 ml) was allowed to heat at 60° C. for 18 hours. The reaction was poured into water (150 ml) and extracted with ethyl ether (2×100 ml). The organic layer was dried over anhydrous sodium sulfate, filtered and the solvent was removed under vacuum to afford an orange solid. The solid was washed with ethyl ether (5 ml) to afford an orange crystalline solid: mp 113–114° C.

Elemental analysis for $C_8H_8N_5O_2Cl$ Calc'd: C, 37.298; H, 3.13, N, 27.19 Found: C, 37.60; H, 2.94; N, 26.98

INTERMEDIATE 46

2-(2-Amino-ethoxy)-4-chloro-6-nitro-phenylamine

A solution of 2-(2-azido-ethoxy)-4-chloro-6-nitro-phenylamine (1.9 g, 7.36 mmol) and triphenylphosphine (2.27 g, 8.65 mmol) in tetrahydrofuran (80 ml) and water (2 ml) was allowed to stir for 24 hours at room temperature. The solvent was removed under vacuum and the solid washed with methylene chloride (30 ml) to afford an orange solid: mp 156–157° C.

Elemental analysis for $C_8H_{10}N_3O_3$ Calc'd: C, 41.48; H, 4.35; N, 18.19 Found: C, 40.01; H, 4.05; N, 16.82

INTERMEDIATE 47

2-{2-[(1,4-trans)-4-(5-Fluoro-1H-indol-3-yl)-cyclohexylamino]-ethoxy}-4-chloro-6-nitro-phenylamine A solution of 2-(2-amino-ethoxy)-4-chloro-6-nitro-phenylanmine (0.8 g, 3.45 mmol), 4-(6-fluoro-1H-indol-3-yl)-cyclohexanone (0.82 g, 3.56 mmol), sodium triacetoxy-borohydride (1.05 g, 4.96 mmol) and acetic acid (0.62 g) in 1,2-dichloroethane (80 ml) was allowed to stir at room temperature for 24 hours. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (10% methanol-ethyl acetate) afforded 0.78 g (85% pure) of product: MS (EI) m/e (M$^+$).

INTERMEDIATE 48

3-{2-[(1,4-trans)-4-(5-Fluoro-1H-indol-3-yl)-cyclohexylamino]-ethoxy}-benzene-5-chloro-1,2-diamine To a mixture of 2-{2-[(1,4-trans)-4-(5-fluoro-1H-indol-3-yl)-cyclohexylamino]-ethoxy}-4-chloro-6-nitro-phenylamine (0.78 g, 1.7 mmol) and Raney nickel (0.76 g) in methanol (40 ml) was slowly added hydrazine monohydrate (1.1 ml). The reaction was allowed to reflux for 0.5 hour. The catalyst was filtered off and the solvent removed under vacuum. Chromatography (10% methanol-ethyl acetate) afforded 0.56 g (90%) of product as a light-yellow foam: MS ESI m/e 417 (M+H)$^+$.

INTERMEDIATE 49

2-(4-Fluoro-phenoxy)-ethylchloride

To a solution of 4-fluorophenol (5.6 g, 50 mmol), triphenylphosphine (19.7 g, 75 mmol), 2-chloroethanol (5.03 ml, 75 mmol) in tetrahydrofuran (100 ml) was slowly added diethyl azodicarboxylate (11.8 ml, 75 mmol). The reaction was stirred at room temperature for 2 hours, and the tetrahydrofuran was removed under vacuum. Chromatography (5% ethyl acetate-hexanes) afforded 6.5 g (75%) of product as a oil: $^1$H NMR (400 MHz, CDCl$_3$): δ3.80 (2H, t, J=5.92 HZ);4.19 (2H, t, J=5.96 Hz); 6.85–6.88 (2H, m); 6.95–7.00 (2H, m).

INTERMEDIATE 50

2-(2-Chloro-ethoxy)-5-fluoro-carbaldehyde

To a solution of 2-(4-fluoro-phenoxy)-ethylchloride (5.23 g, 30 mmol) in anhydrous methylene chloride (20 ml) was slowly added TiCl$_4$ (5.61 g, 51 mmol) and α,α'-dichloromethyl methyl ether (2.77 g, 30 mmol) at 0° C. The reaction was allowed to reach room temperature slowly and was stirred for 2 hours. The reaction mixture was poured into ice-water, extracted with methylene chloride (3×100 ml) and washed sequentially with saturated sodium carbonate (5×150 ml) and brine (3×100 ml). The organic layer was dried over anhydrous sodium sulfate, filtered, and the solvent was removed under vacuum. Chromatography (20% ethyl acetate-hexanes) afforded 5.5 g (59%) of product as a oil: MS (EI) 202/204 m/e (M$^+$).

INTERMEDIATE 51

2-(4-Fluoro-2-hydroxy-phenoxy)ethylazide

To a solution of 2-(2-chloro-ethoxy)-5-fluoro-carbaldehyde (6.0 g, 29.6 mmol), 3-t-butyl-4-hydroxy-5-methylphenyl sulfide (100 mg) in anhydrous methylene chloride (60 ml) at 0° C. was added 3-chloroperoxybenzoic acid (mCPBA) (10.9 g) portionwise. The reaction mixture was allowed to reflux for 16 hours. The excess mCBPA was destroyed by adding 10% sodium sulfite. The benzoic acid was filtered and the filtrate was extracted with methylene chloride (3×150 ml) and washed with water (3×150 ml). The organic layer was dried over anhydrous sodium sulfate and filtered. The solvent was removed under vacuum to afford a crude product 4.8 g (22 mmol) which was dissolved in anhydrous N,N-dimethylformamide (30. ml). To above solution was added sodium azide (4.3 g, 66 mmol). The mixture was allowed to heat at 60° C. for 18 hours. The reaction was poured into water (150 ml) and extracted with ethyl ether (2×100 ml). The organic layer was dried over anhydrous sodium sulfate, and the solvent was removed under vacuum. Chromatography (20% ethyl acetate-hexanes) afforded 0.8 g of product as a oil.

INTERMEDIATE 52

2-(4-Fluoro-2-methoxy-phenoxy)ethylamine

To a solution of 2-(4-fluoro-2-hydroxy-phenoxy) ethylazide (0.8 g, 4.06 mmol), triphenylphosphine (3.2 g, 12.2 mmol), methanol (0.5 ml, 12.2 mmol) in dioxane (15 ml) was slowly added diethyl azodicarboxylate (1.9 ml, 12.2 mmol). The reaction was stirred at room temperature for 2 hours. The solvent was removed under vacuum. Chromatography (20% ethyl acetate-hexanes) afforded 0.6 g (70%) of product as a oil, which was dissolved in tetrahydrofuran (15 ml) and water (0.06 ml). To the above solution was added triphenylphosphine (1.04 g, 2.8 mmol), and the mixture was allowed to stir for 18 hours at room temperature. The solvent was removed under vacuum. Chromatography (90% ethyl acetate-methanol plus ammonium hydroxide) afforded 0.43 g (80%) of product as a clear oil: MS (EI) 185 m/e (M$^+$).

INTERMEDIATE 53a

3-[4-(Methoxymethylene)cyclohexyl]-5-fluoro-1H-indole

To a suspension of (methoxymethyl) triphenylphosphonium chloride in tetrahydrofuran (26 ml) was added n-butyllithium (5.2 ml, 13 mmol) at −78° C. The mixture was allowed to stir for 20 minutes at 78° C., then a solution of 4-(5-fluoro-1H-3-indolyl)-cyclohexanone (1.5 g, 6.5 mmol) was added. After addition, the reaction mixture was warmed to −10° C., and allowed to stir for 2 hours. The mixture was quenched with saturated ammonium chloride and diluted with ethyl acetate. The organic layer was separated, dried over anhydrous sodium sulfate and filtered. Chromatography (25% ethyl acetate-hexanes) afforded 0.61 g (36%) of product as a clear oil: MS (EI) 259 m/e (M$^+$).

INTERMEDIATE 53b

3-[4-(Methoxymethylene)cyclohexyl]-5-cyano-1H-indole

The above compound was prepared in the manner described for (53a) using 4-(5-cyano-1H-3-indolyl)- cyclohexanone (3c) to obtain in 30% yield (2.8 g) of product as a white solid: MS (+ESI) 267 m/e (M+H)$^+$.

INTERMEDIATE 54a cis- and trans-4-(5-Fluoro-1H-indol-3-yl)cyclohexanecarbaldehyde To a solution of 3-[4-(methoxymethylene)cyclohexyl]-5-fluoro-1H-indole in methanol (3 ml) was added 1N HCl (40 ml) at room temperature. The mixture was allowed to reflux for 30 minutes, whereby an oil precipitated. To the above mixture was added acetone (10 ml), and the mixture was allowed to reflux for another 30 min and cooled to room temperature. The mixture was extracted with ethyl acetate, dried over anhydrous sodium sulfate and filtered. The solvent was removed under vacuum to afford 0.4 g of the title compound.

INTERMEDIATE 54b cis- and trans-4-(5-Cyano-1H-indol-3-yl)cyclohexanecarbaldehyde The compound was prepared in the manner described for Intermediate (54a) using Intermediate 53b to obtain the product in 6% yield (0.15 g).

INTERMEDIATE 55, 56

2-Methoxy-4,5-difluoro-phenol (55)

2-Methoxy-4-methylthio-5-fluoro-phenol (56)

To a solution of 1,2-difluoro-4,5-dimethoxybenzene (2.61 g, 15 mmol) in N,N-dimethylformamide (20 ml) was added sodium thiomethoxide (95%, 1.11 g, 15 mmol). The reaction was allowed to reflux for 3 hours and then was cooled to room temperature. The mixture was poured into 200 ml ice-water and neutralized with 2 N HCl. The aqueous layer was extracted with ethyl ether (2×100 ml), washed with water, dried over anhydrous sodium sulfate and filtered. The solvent was removed under vacuum to afford a mixture of the two title products.

INTERMEDIATE 57, 62

1,2-Difluoro-4-(2-chloroethoxy)-5-methoxy-benzene (57)

1-Fluoro-2-methylthio-4-(2-chloroethoxy)-5-methoxy-benzene (62)

To a solution of a mixture of 2-methoxy-4,5-difluorophenol (Intermediate 55) and 2-methoxy-4-methylthio-5-fluoro-phenol (Intermediate 56) (0.66 g), triphenylphosphine (2.16 g), 2-chloroethanol (0.55 ml) in tetrahydrofuran (15 ml) was slowly added diethyl azodicarboxylate (1.3 ml). The reaction was stirred at room temperature for 2 hours. Tetrahydrofuran was removed under vacuum. Chromatography (10% ethyl acetate-hexanes) afforded 0.31 g of 1,2-difluoro-4-(2-chloroethoxy)-5-methoxy-benzene (Intermediate 57) as a white solid: mp 51–52° C.; MS EI m/e 222 (M$^+$), and 0.1 g of 1-fluoro-2-methylthio-4-(2-chloroethoxy)-5-methoxy-benzene (Intermediate 62) as a white solid: mp 58–60° C.; MS EI m/e 250 (M$^+$).

INTERMEDIATE 58

2-(2-Methoxy-4,5-difluoro-phenoxy)-ethylazide

To a solution of 1,2-difluoro-4-(2-chloroethoxy)-5-methoxy-benzene (0.77 g, 3.46 mmol) in N,N-dimethylformamide (30 ml) was added sodium azide (0.67 g, 10.4 mmol). The mixture was allowed to heat at 60° C. for 18 hours. The reaction was poured into water (150 ml) and extracted with ethyl ether (2×100 ml). The organic layer was dried over anhydrous sodium sulfate, filtered and the solvent was removed under vacuum. Chromatography (20% ethyl acetate-hexanes) afforded 0.69 g of product as a oil.

INTERMEDIATE 59

2-(2-Methoxy-4,5-difluoro-phenoxy)-ethylamine

A solution of 2-(2-methoxy-4,5-difluoro-phenoxy)-ethylazide (0.69 g, 3.46 mmol) and triphenylphosphine (1.27 g, 4.84 mmol) in tetrahydrofuran (15 ml) containing water (0.08 ml) was stirred at room temperature overnight. The solvent was removed under vacuum. Chromatography with ethyl acetate removed triphenylphosphine oxide, followed elution with ethyl acetate-methanol-ammonium hydroxide 8.5:1.5:0.5, afforded 0.53 g of product as a white solid: mp 44–46° C.; MS EI m/e 203 (M$^+$).

INTERMEDIATE 60

(trans)-4-(5-Fluoro-1H-indol-3-yl)-cyclohexyl-benzyl Amine

A solution of 4-(5-fluoro-1H-indol-3-yl)-cyclohexanone (2.31 g, mmol), benzylamine (1.1 g, 10 mmol), sodium triacetoxyborohydride (3.1 g, 14 mmol) and acetic acid (0.57 ml) in 1,2-dichloroethane (30 ml) was allowed to stir at room temperature for 4 hours. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (ethyl acetate-hexanes-methanol-ammonium hydroxide: 50:50:5:0.5) afforded 0.51 g (16%) of product as a white solid: mp 131–133° C. MS EI m/e 322 (M$^+$)

INTERMEDIATE 61

(trans)-4-(5-Fluoro-1H-indol-3-yl)-cyclohexyl-amine

A mixture of (trans)-4-(5-fluoro-1H-indol-3-yl)-cyclohexyl-benzyl amine (0.24 g, 0.74 mmol) and 10% palladium on carbon (0.1 g) in ethanol (30 ml) was hydrogenated overnight. The catalyst was filtered off and the solvent removed under vacuum. Chromatography (ethyl acetate-methanol-ammonium hydroxide: 9:1:0.1) afforded 0.17 g (100%) of product as a white solid: mp 198–200° C.; MS EI m/e 232 (M$^+$).

INTERMEDIATE 63

1-Fluoro-2-methylsulfonyl-4-methoxy-5-(2-chloroethoxy)-benzene

To a solution of 1-fluoro-2-methylthio-4-(2-chloroethoxy)-5-methoxy-benzene in tetrahydrofuran (20 ml) was added 3-chloroperoxybenzoic acid (mCPBA) (1.07 g). The mixture was allowed to stir overnight at room temperature and quenched with Na$_2$S$_2$O$_5$. The mixture was diluted with ethyl acetate and washed with sodium bicarbonate and water. The organic layer was separated, dried over anhydrous sodium sulfate and filtered. Chromatography (30% ethyl acetate—hexanes) afforded 0.19 g of product as a white solid: mp 85–87° C.; MS EI m/e 282 (M$^+$).

INTERMEDIATE 64

5-Fluoro-3-(1-oxa-sprio[2,5]oct-6-yl)-1H-indole

To a suspension of trimethylsulfoxonium iodide (1.3 g, 6 mmol) in tetrahydrofuran (15 ml) was added sodium hydride (60%, 0.24 g, 6 mmol) at room temperature. The reaction mixture was allowed to reflux for 1 hour. The mixture was cooled to room temperature, followed by addition of 4-(5-fluoro-1H-3-indolyl)-cyclohexanone in tetrahydrofuran (5 ml) to above solution. After stirring for 2 hours at room temperature, the mixture was quenched with ammonium chloride and diluted with ethyl acetate. The organic layer was washed with water, dried over anhydrous sodium sulfate and filtered. Chromatography (30% ethyl acetate-hexanes) afforded 0.45 g (92%) of product as a white solid: mp 108–110° C.; MS EI m/e 245 (M$^+$).

EXAMPLE 1a

[(cis)-4-(5-Fluoro-1H-indol-3-yl)-cyclohexyl]-[2-(2-methoxy-phenoxy)-ethyl]-amine A solution of 4-(5-fluoro-1H-indol-3-yl)-cyclohexanone (0.38 g, 1.6 mmol), [2-(2-methoxy-phenoxy)-ethyl]-amine (0.27 g, 1.6 mmol), sodium triacetoxyborohydride (0.5 g, 2.2 mmol) and acetic acid (0.06 ml, 1.8 mmol) in 1,2-dichloroethane (8 ml) was allowed to stir at room temperature for 4 hours. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (10% methanol-ethyl acetate) afforded 0.43 g (71%) of product as a white solid.

The HCl salt was prepared in ethyl acetate: mp 186–188° C.

Elemental analysis for $C_{23}H_{27}FN_2O_2 \cdot HCl \cdot 0.06C_4H_8O_2$ Calc'd: C, 65.80; H, 6.77; N, 6.60 Found: C, 65.59; H, 6.69; N, 6.44

EXAMPLE 1b

[(trans)-4-(5-Fluoro-1H-indol-3-yl)-cyclohexyl]-[2-(2-methoxy-phenoxy)-ethyl]-amine The trans compound was isolated at same time as the cis isomer (Example 1a) in 19% yield (0.115 g) as a white solid.

The fumatate salt was prepared in isopropanol: mp 228–230° C.

Elemental analysis for $C_{23}H_{26}F_2N_2O_2 \cdot 0.5C_4H_4O_4$ Calc'd: C, 67.47; H, 6.68; N, 6.29 Found: C, 67.22; H, 6.53; N, 6.14

EXAMPLE 2a

[(1,4-cis)-4-(6-Fluoro-1H-indol-3-yl)-cyclohexyl]-[2-(5-fluoro-2-methoxy-phenoxy)-ethyl]-amine A solution of 4-(6-fluoro-1H-indol-3-yl)-cyclohexanone (0.62 g, 2.7 mmol), [2-(5-fluoro-2-methoxy-phenoxy)-ethyl]-amine (0.5 g, 2.7 mmol), sodium triacetoxyborohydride (0.86 g, 4 mmol) and acetic acid (0.32 g, 5.4 mmol) in 1,2-dichloroethane (20 ml) was allowed to stir at room temperature for 16 hours. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (10% methanol-ethyl acetate) afforded 0.75 g (73%) of product as a clear oil.

The oxalate salt was prepared in ethanol: mp 145–146.5° C.

Elemental analysis for $C_{23}H_{26}F_2N_2O_2 \cdot HCl \cdot 0.5H_2O$ Calc'd: C,61.95; H, 6.33; N, 6.28 Found: C, 62.02; H, 6.28; N, 5.87

EXAMPLE 2b

[(1,4-trans)-4-(6-Fluoro-1H-indol-3-yl)-cyclohexyl]-[2-(5-fluoro-2-methoxy-phenoxy)-ethyl]-amine The trans compound was isolated at same time as the cis isomer in 14% yield (0.15 g) as a clear oil.

The oxalate salt was prepared in ethanol: mp 162–164° C.

Elemental analysis for $C_{23}H_{26}F_2N_2O_2 \cdot 1.5C_2H_2O_4$ Calc'd: C, 58.31; H, 5.46; N, 5.23 Found: C, 58.58; H, 5.27; N, 5.33

EXAMPLE 3a

[(Cis)-4-(5-Fluoro-1H-indol-3-yl)-cyclohexyl]-[2-(2-(1H-indol-4-yloxy)ethyl]-amine A solution of 4-(5-fluoro-1H-indol-3-yl)-cyclohexanone (0.87 g, 3.75 mmol), [2-(1H-indol-4-yloxy)-ethyl]-amine (0.66 g, 3.75 mmol), sodium triacetoxyborohydride (1.17 g, 5.25 mmol) and acetic acid (0.22 ml, 3.75 mmol) in 1,2-dichloroethane (17 ml) was allowed to stir at room temperature for 5 hours. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (2% methanol-ethyl acetate plus 0.2% ammonium hydroxide) afforded 0.71 g (48%) of product as a solid: mp 74–76° C.

The fumarate salt was prepared in ethanol: mp 148–150° C.

Elemental analysis for $C_{24}H_{26}FN_3O \cdot 0.5C_4H_4O_4 \cdot 0.5C_3H_8O$ Calc'd: C, 68.23; H, 6.77; N, 8.68 Found: C, 68.07; H, 6.75; N, 8.43

EXAMPLE 3b

[(Trans)-4-(5-Fluoro-1H-indol-3-yl)-cyclohexyl]-[2-(2-(1H-indol-4-yloxy) ethyl]-amine The trans compound was isolated at same time as the cis isomer (Example 3a) in 11% yield (0.16 g) as a white solid: mp 78–80° C.

The fumarate salt was prepared in isopropanol: mp 245° C. (decomposed).

Elemental analysis for $C_{24}H_{26}FN_3O \cdot 0.5C_4H_4O_4$ Calc'd: C, 68.78; H, 6.33; N, 9.25 Found: C, 68.66; H, 6.31; N, 9.04

EXAMPLE 3c

[(Cis)-4-(1H-indol-3-yl)-cyclohexyl]-[2-(2-(1H-indol-4-yloxy)ethyl]-amine

A solution of 4-(1H-indol-3-yl)-cyclohexanone (0.42 g, 1.99 mmol), [2-(1H-indol-4-yloxy)-ethyl]-amine (1.99 mmol), sodium triacetoxyborohydride (0.62 g, 2.79 mmol) and acetic acid (0.11 ml, 1.99 mmol) in 1,2-dichloroethane (10 ml) was allowed to stir at room temperature for 5 hours. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (methanol-ethyl acetate-hexanes-ammonium hydroxide 5:5:0.5:0.1) afforded 0.11 g of product.

The HCl salt was prepared in ethyl acetate: mp 157° C. (decomposed).

Elemental analysis for $C_{24}H_{27}N_3OHCl$ Calc'd: C, 66.65; H, 7.11; N, 9.72 found: C, 66.91; H, 6.89; N, 9.52

EXAMPLE 3d

[(Trans)-4-(1H-Indol-3-yl)-cyclohexyl]-[2-(2-(1H-indol-4-loxy)ethyl]-amine

The trans compound was isolated at same time as the cis isomer (Example 3c) in 14% yield (0.12 g).

The HCl salt was prepared in ethyl acetate: mp 249° C. (decomposed).

Elemental analysis for $C_{24}H_{27}N_3O.HCl$ Calc'd: C, 68.80; H, 6.98; N, 10.03 Found: C, 68.74; H, 6.88; N, 10.03

EXAMPLE 4a

[2-(2,3)-Dihydro-benzo[1,4]dioxin-5-yloxy)-ethyl]-[(1,4-cis)-4-(5-fluoro-1H-indol-3-yl)-cyclohexyl]-amine A solution of 4-(5-fluoro-1H-indol-3-yl)-cyclohexanone (0.78 g, 3.4 mmol), [2-(2,3)-dihydro-benzo[1,4]dioxin-5-yloxy)]-ethyl-amine (0.66 g, 3.4 mmol), sodium triacetoxyborohydride (1.08 g, 5 mmol) and acetic acid (0.3 g, 5.1 mmol) in 1,2-dichloroethane (50 ml) was allowed to stir at room temperature for 4 hours. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (10% methanol-ethyl acetate plus 0.2% ammonium hydroxide) afforded 0.67 g (48%) of product as a clear oil.

The oxalate salt was prepared in ethanol: mp 193–194° C.

Elemental analysis for $C_{24}H_{27}FN_2O_3.C_2H_2O_4$ Calc'd: C, 62.35; H, 5.84; N, 5.59 Found: C, 62.09; H, 5.86; N, 5.41

EXAMPLE 4b

[2-(2,3)-Dihydro-benzo[1,4]dioxin-5-yloxy)-ethyl]-[(1,4-trans)-4-(5-fluoro-1H-indol-3-yl)-cyclohexyl]-amine The trans compound was isolated at same time as the cis isomer (Example 4a) in 12% yield (0.16 g) as a clear oil.

The oxalate salt was prepared in ethanol: mp 197.5–199.5° C.

Elemental analysis for $C_{24}H_{27}FN_2O_3.C_2H_2O_4.0.5H_2O$ Calc'd: C, 61.29; H, 5.94; N, 5.50 Found: C, 61.47; H, 5.87; N, 5.22

EXAMPLE 4c

[2-(2,3)-Dihydro-benzo[1,4]dioxin-5-yloxy)-ethyl]-[(1,4-cis)-4-(6-fluoro-1H-indol-3-yl)-cyclohexyl]-amine A solution of 4-(6-fluoro-1H-indol-3-yl)-cyclohexanone (0.71 g, 3.1 mmol), [2-(2,3)-dihydro-benzo[1,4]dioxin-5-yloxy)]-ethyl-amine (0.6 g, 3.1 mmol), sodium triacetoxyborohydride (0.98 g, 4.6 mmol) and acetic acid (0.37 g, 6.1 mmol) in 1,2-dichloroethane (30 ml) was allowed to stir at room temperature for 4 hours. The reaction was quenched with 1N sodium hydroxide (20 ml), extracted with methylene chloride (3×100 ml), and washed with brine (3×100 ml). The organic layer was dried over anhydrous sodium sulfate and filtered. Chromatography (10% methanol-ethyl acetate plus 0.2% ammonium hydroxide) afforded 0.83 g (58%) of product as a clear oil.

The oxalate salt was prepared in ethanol: mp 179–180° C.

Elemental analysis for $C_{24}H_{27}FN_2O_3.C_2H_2O_4$ Calc'd: C, 62.35; H, 5.84; N, 5.59 Found: C, 62.22; H, 5.89; N, 5.46

EXAMPLE 4d

[2-(2,3)-Dihydro-benzo[1,4]dioxin-5-yloxy)-ethyl]-[(1,4-trans)-4-(6-fluoro-1H-indol-3-yl)-cyclohexyl]-amine The trans compound was isolated at same time as the cis isomer (Example 4c) in 17% yield (0.24 g) as a clear oil.

The oxalate salt was prepared in ethanol: mp 180–181.5° C.

Elemental analysis for $C_{24}H_{27}FN_2O_3.C_2H_2O_4.0.25H_2O$ Calc'd: C, 61.34; H, 6.26; N, 5.26 Found: C, 61.06; H, 6.31; N, 5.01

EXAMPLE 5a

[2-(6-Fluoro-chroman-8-yloxy)-ethyl]-[(1,4-cis)-4-(5-fluoro-1H-indol-3-yl)-cyclohexyl]-amine A solution of 4-(5-fluoro-1H-indol-3-yl)-cyclohexanone (0.46 g, 2.4 mmol), 2-(6-fluorochroman-8-yloxy)ethylamine (0.5 g, 2.4 mmol), sodium triacetoxyborohydride (0.75 g, 3.6 mmol) and acetic acid (0.28 g, 4.7 mmol) in 1,2-dichloroethane (20 ml) was allowed to stir at room temperature for 16 hours. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (10% methanol-ethyl acetate) afforded 0.65 g (64%) of product as a clear oil.

The HCl salt was prepared in ethanol: mp 142–143° C.

Elemental analysis for $C_{23}H_{26}F_2N_2O_2.HCl$ Calc'd: C, 64.86; H, 6.31; N, 6.05 Found: C, 65.32; H, 6.30; N, 6.06

EXAMPLE 5b

[2-(6-Fluoro-chroman-8-yloxy)-ethyl]-[(1,4-trans)-4-(5-fluoro-1H-indol-3-yl)-cyclohexyl]-amine The trans compound was isolated at same time as the cis isomer (Example 5a) in 19% yield (0.19 g) as a clear oil.

The oxalate salt was prepared in ethanol: mp 172–174° C.

Elemental analysis for $C_{25}H_{28}F_2N_2O_2.C_2H_2O_4.0.5H_2O$ Calc'd: C, 61.70; H, 5.95; N, 5.33 Found: C, 61.38; H, 6.10; N, 5.15

EXAMPLE 5c

3-{(1,4-cis)-4-[2-(6-Fluoro-chroman-8-yloxy)-ethylamino]-cyclohexyl}-1-methyl-1H-indole-5-carbonitrile This compound was prepared in the manner as described above for Example 5a by replacing 4-(5-fluoro-1H-indol-3-yl)-cyclohexanone with 4-(5-cyano-1-methyl-3-indolyl)-cyclohexanone (0.6 g, 2.8 mmol) to obtain 38% (0.41 g) of product as a clear oil.

The oxalate salt was prepared in ethanol: mp 190–191° C.

Elemental analysis for $C_{27}H_{30}FN_3O_2.C_2H_2O_4$ Calc'd: C, 64.79; H, 6.00; N, 7.82 Found: C, 64.70; H, 6.02; N, 7.60

EXAMPLE 5d

3-{(1,4-cis)-4-[2-(6-Fluoro-chroman-8-yloxy)-ethylamino]-cyclohexyl}-1-methyl-1H-indole-5-carbonitrile The trans compound was isolated at same time as the cis isomer (Example 5c) in 13% yield (0.14 g) as a clear oil.

The oxalate salt was prepared in ethanol: mp 199–213° C.

Elemental analysis for $C_{27}H_{30}FN_3O_2 \cdot C_2H_2O_4 \cdot 0.5H_2O$
Calc'd: C, 63.72; H, 6.09; N, 7.69 Found: C, 63.72; H, 5.80; N, 8.24

EXAMPLE 5e

3-{(1,4-cis)-4-[2-(6-Fluoro-chroman-8-yloxy)-ethylamino]-cyclohexyl}-1H-indole-5-carbonitrile This compound was prepared in the manner as described above for Example 5a by replacing 4-(5-fluoro-1H-indol-3-yl)-cyclohexanone with 4-(5-cyano-3-indolyl)-cyclohexanone (0.32 g, 1.3 mmol) to obtain 44% (0.25 g) of product.

The oxalate salt was prepared in ethanol: mp 217–219° C.

Elemental analysis for $C_{26}H_{28}FN_3O_2 \cdot C_2H_2O_4$ Calc'd: C, 64.20; H, 5.77; N, 8.02 Found: C, 64.00; H, 6.17; N, 7.87

EXAMPLE 5f

3-{(1,4-trans)-4-[2-(6-Fluoro-chroman-8-yloxy)-ethylamino]-cyclohexyl}-1H-indole-5-carbonitrile The trans compound was isolated at same time as the cis (5e) isomer in 25% yield (0.14 g) as a white solid: mp 129–131° C.

The oxalate salt was prepared in ethanol: mp 88–90° C.
Elemental analysis for $C_{26}H_{28}FN_3O_2 \cdot C_2H_2O_4 \cdot 0.25C_2H_6O \cdot H_2O$ Calc'd: C, 61.89; H, 6.16; N, 7.60 Found: C, 62.17; H, 6.19; N, 7.31

EXAMPLE 6a

3-{(1,4-cis)-4-[2-(5-Fluoro-2,3-dihydro-benzofuran-7-yloxy)ethylamino]-cyclohexyl]}-1H-indole-5-carbonitrile A solution of 4-(5-cyano-1H-indol-3-yl)-cyclohexanone (0.6 g, 2.5 mmol), 2-(5-fluoro-2,3-dihydrofuran-7-yloxy) ethylamine (0.5 g, 2.5 mmol), sodium triacetoxyborohydride (0.81 g, 3.8 mmol) and acetic acid (0.30 g, 5.1 mmol) in 1,2-dichloroethane (20 ml) was allowed to stir at room temperature for 16 hours. The reaction was quenched with 1N sodium hydroxide (20 ml), extracted with methylene chloride (3×100 ml) and washed with brine (3×100 ml). The organic layer was dried over anhydrous sodium sulfate and filtered. Chromatography (10% methanol-ethyl acetate) afforded 0.6 g (56%) of product as a white solid: mp 152.5–154° C.

The oxalate salt was prepared in ethanol: mp 179–180.5° C.

Elemental analysis for $C_{25}H_{26}FN_3O_2 \cdot C_2H_2O_4$ Calc'd: C, 63.61; H, 5.54; N, 8.24 Found: C, 63.38; H, 5.50; N, 8.26

EXAMPLE 6b

3-{(1,4-trans)-4-[2-(5-Fluoro-2,3-dihydro-benzofuran-7-yloxy)ethylamino]-cyclohexyl]}-1H-indole-5-carbonitrile The trans compound was isolated at same time as the cis isomer (Example 6a) in 27% yield (0.29 g) as a white solid: mp 190–190.5° C.

The oxalate salt was prepared in ethanol: mp 172–174° C.

Elemental analysis for $C_{25}H_{26}FN_3O_2 \cdot C_2H_2O_4 \cdot 0.5H_2O$ Calc'd: C, 62.54; H, 5.64; N, 8.01 Found: C, 62.38; H, 5.65; N, 7.97

EXAMPLE 7a

[2-(5-Fluoro-benzofuran-7-yloxy)-ethyl]-[(1,4-cis)-4-(5-fluoro-1H-indol-3-yl)-cyclohexyl]-amine A solution of 4-(5-fluoro-1H-indol-3-yl)-cyclohexanone (0.72 g, 3.1 mmol), 2-(5-fluoro-benzofuran-7-yloxy) ethylamine (0.55 g, 2.82 mmol), sodium triacetoxyborohydride (0.84 g, 3.94 mmol) and acetic acid (0.18 g, 2.82 mmol) in 1,2-dichloroethane (20 ml) was allowed to stir at room temperature for 16 hours. The reaction was quenched with 0.5 N sodium hydroxide (100 ml), extracted with methylene chloride (2×100 ml) and washed with brine (2×100 ml). The organic layer was dried over anhydrous magnesium sulfate and filtered. The solvent was removed under vacuum and crystals appeared after 1 hour. The product was triturated with ethyl ether (80 ml) to afford 0.27 g of product. The mother liquor was concentrated and diluted with ethyl ether to afford another 0.2 g of product.

The oxalate salt was prepared in ethanol: mp 173–174° C.

Elemental analysis for $C_{24}H_{24}F_2N_2O_2 \cdot C_2H_2O_4$ Calc'd: C, 63.61; H, 5.54; N, 8.24 Found: C, 63.38; H, 5.50; N, 8.26

EXAMPLE 7b

[2-(5-Fluoro-benzofuran-7-yloxy)-ethyl]-[(1,4-trans)-4-(5-fluoro-1H-indol-3-yl)-cyclohexyl]-amine The trans compound was isolated by chromatography from the residue remaining in Example 7a (3:5:3 acetone-methanol-hexanes) to afford 0.17 g of product as a glass.

The oxalate salt was prepared in ethanol: mp 221–223° C.

Elemental analysis for $C_{24}H_{24}F_2N_2O_2 \cdot C_2H_2O_4$ Calc'd: C, 62.40; H, 5.24; N, 5.60 Found: C, 62.98; H, 5.28; N, 5.36

EXAMPLE 8a

[2-(6-Chloro-1H-benzoimidazol-4-yloxy)-ethyl]-[(1,4-trans)-4-(5-fluoro-1H-indol-3-yl)-cyclohexyl]-amine A solution of [2-(2,3-diamino-5-fluoro-phenoxy)-ethyl]-[(1,4-trans)-4-(5-fluoro-1H-indol-3-yl)-cyclohexyl]-amine (0.25 g) in formic acid (15 ml) was allowed to reflux for 3 hours. The mixture was poured into 1N sodium hydroxide, extracted with ethyl acetate (3×100 ml) and washed with 1N sodium hydroxide (3×100 ml). The organic layer was dried over anhydrous sodium sulfate and filtered. Chromatography (10% methanol-methylene chloride plus ammonium hydroxide) afforded 0.14 g (39%) of product as a clear oil.

The oxalate salt was prepared in isopropanol: mp 162–165° C.

Elemental analysis for $C_{23}H_{24}ClFN_4O \cdot C_2H_2O_4 \cdot 0.25H_2O$ Calc'd: C, 53.03; H, 4.70; N, 9.16 Found: C, 52.87; H, 4.58; N, 9.54

EXAMPLE 8b

[2-(6-Chloro-2-methyl-1H-benzoimidazol-4-yloxy)-ethyl]-[(1,4-trans)-4-(5-fluoro-1H-indol-3-yl)-cyclohexyl]-amine A solution of [2-(2,3-diamino-5-fluoro-phenoxy)-ethyl]-[(1,4-trans)-4-(5-fluoro-1H-indol-3-yl)-cyclohexyl]-amine (0.15 g) in acetic acid (15 ml) was allowed to reflux for 18 hours. The mixture was poured into saturated sodium bicarbonate and extracted with methylene chloride (2×150 ml). The organic layer was dried over anhydrous magnesium sulfate and filtered. Chromatography (7% methanol-methylene chloride plus 1% ammonium hydroxide) afforded 0.10 g of product as a yellow solid: mp 185–187° C.

The oxalate salt was prepared in ethanol: mp 204–205.5° C.

Elemental analysis for $C_{24}H_{26}ClFN_4O.2C_2H_2O_4$ Calc'd: C, 54.15; H, 4.87; N, 9.02 Found: C, 53.94; H, 5.21; N, 8.87

EXAMPLE 9a

[(1,4-cis)-4-(5-Fluoro-1H-indol-3-yl)-cyclohexyl]-[2-(4-fluoro-2-methoxy-phenoxy)-ethyl]-amine A solution of 4-(5-fluoro-1H-indol-3-yl)-cyclohexanone (0.41 g, 1.78 mmol), 2-(4-fluoro-2-methoxy-phenoxy) ethylamine (0.33 g, 1.78 mmol), sodium triacetoxyborohydride (0.56 g, 2.49 mmol) and acetic acid (0.1 ml) in 1,2-dichloroethane (10 ml) was allowed to stir at room temperature for 16 hours. The reaction was quenched with 0.5 N sodium hydroxide (100 ml), extracted with methylene chloride (2×100 ml) and washed with brine (2×100 ml). The organic layer was dried over anhydrous magnesium sulfate and filtered. The solvent was removed under vacuum. Chromatography (2% methanol-ethyl acetate plus 0.2% ammonium hydroxide) afforded 0.4 g (56%) of product as a white foam.

The HCl salt was prepared in ethyl acetate: mp 150–152° C.

Elemental analysis for $C_{23}H_{26}F_2N_2O_2.HCl$ Calc'd: C, 62.58; H,6.28; N, 6.35 Found: C, 62.72; H,6.34; N, 6.27

EXAMPLE 9b

[(1,4-trans)-4-(5-Fluoro-1H-indol-3-yl)-cyclohexyl]-[2-(4-fluoro-2-methoxy-phenoxy)-ethyl]-amine The trans compound was isolated at same time as the cis isomer (Example 9a) in 15% yield (0.11 g) as a white foam.

The HCl salt was prepared in ethyl acetate: mp 188–190° C.

Elemental analysis for $C_{23}H_{26}F_2N_2O2.HCl$ Calc'd: C, 62.58; H, 6.28; N, 6.35 Found: C, 62.83; H, 6.18; N, 6.22

EXAMPLE 10a

[(1,4-trans)-4-(5-Fluoro-1H-indol-3-yl)-cyclohexylmethyl]-[2-(2-methoxy-phenoxy)-ethyl]-amine A solution of 4-(5-fluoro-1H-indol-3-yl) cyclohexanecarbaldehyde (0.25 g, 1.02 mmol), 2-(2-methoxy-phenoxy)ethylamine (0.17 g, 1.02 mmol), sodium triacetoxyborohydride (0.32 g, 1.4 mmol) and acetic acid (0.06 ml) in 1,2-dichloroethane (5 ml) was allowed to stir at room temperature for 16 hours. The reaction was quenched with 0.5 N sodium hydroxide (100 ml), extracted with methylene chloride (2×100 ml) and washed with brine (2×100 ml). The organic layer was dried over anhydrous magnesium sulfate and filtered. The solvent was removed under vacuum. Chromatography (2% methanol-ethyl acetate plus 0.2% ammonium hydroxide) afforded 0.1 g (25%) of product.

The HCl salt was prepared in ethyl acetate: mp 157–159° C.

Elemental analysis for $C_{24}H_{29}FN_2O_2.HCl$ Calc'd: C, 65.22; H, 7.07; N, 6.34 Found: C, 65.10; H, 6.84; N, 6.25

EXAMPLE 10b 3-(4-{[2-(Methoxy-phenoxy)-ethylamino]-methyl}-cyclohexyl)-1H-indole-5-carbonitrile The compound was prepared in a similar fashion described above using 4-(5-cyano-1H-indol-3-yl) cyclohexanecarbaldehyde in 50% yield (0.08 g) of product.

The HCl salt was prepared in ethyl acetate: mp 50° C. (decomposed).

Elemental analysis for $C_{25}H_{29}N_3O_2.HCl$ Calc'd: C, 63.68; H, 7.16; N, 8.91 Found: C, 63.66; H, 6.80; N, 8.73

EXAMPLE 11a (1,4-cis)-[2-(4,5-Difluoro-2-methoxy-phenoxy)-ethyl]-[4-(5-fluoro-1H-indol-3-yl)-cyclohexyl]-amine A solution of 4-(5-fluoro-1H-indol-3-yl)-cyclohexanone (0.41 g, 1.78 mmol), 2-(2-methoxy--4,5-difluoro-phenoxy)-ethylamine (0.36 g, 1.78 mmol), sodium triacetoxyborohydride (0.56 g, 2.49 mmol) and acetic acid (0.1 ml) in 1,2-dichloroethane (10 ml) was allowed to stir at room temperature for 16 hours. The reaction was quenched with 0.5 N sodium hydroxide (100 ml), extracted with methylene chloride (2×100 ml) and washed with brine (2×100 ml). The organic layer was dried over anhydrous magnesium sulfate and filtered. The solvent was removed under vacuum. Chromatography (2% methanol-ethyl acetate plus 0.2% ammonium hydroxide) afforded 0.38 g (41%) of product.

The HCl salt was prepared in ethyl acetate: mp 98–100° C.

Elemental analysis for $C_{23}H_{25}F_3N_2O_2.HCl$ Calc'd: C, 58.97; H, 5.92; N, 5.98 Found: C, 58.76; H, 5.84; N, 5.79

EXAMPLE 11b (1,4-trans)-[2-(4,5-Difluoro-2-methoxy-phenoxy)-ethyl]-[4-(5-fluoro-1H-indol-3-yl)-cyclohexyl]-amine The trans compound was isolated at same time as the cis isomer (Example 11a) in 16% yield (0.15 g) of product.

The HCl salt was prepared in ethyl acetate: mp 225–227° C.

Elemental analysis for $C_{23}H_{25}F_3N_2O_2.HCl$ Calc'd: C, 57.32; H, 6.07; N, 5.81 Found: C, 57.91; H, 55.94; N, 5.72

EXAMPLE 12

[(1,4-trans)-4-(5-Fluoro-1H-indol-3-yl)-cyclohexyl]-[2-(5-fluoro-4-methanesulfonyl-2-methoxy-phenoxy)-ethyl]-amine A solution of 1-fluoro-2-methylsulfonyl-4-methoxy-5-(2-chloro-ethoxy)-benzene (0.14 g, 0.5 mmol), (trans)-4-(5-fluoro-1H-indol-3-yl)-cyclohexyl-amine (0.11 g, 0.5 mmol) and triethylamine (0.28 ml) in anhydrous dimethylsulfoxide (10 ml) was allowed to stir for 12 hours at 90° C. The mixture was poured into water (100 ml) and extracted with methylene chloride (3×100 ml). The organic layer was washed with water (3×100 ml), dried over anhydrous sodium sulfate, filtered and the solvent was removed under vacuum. Chromatography (7% methanol-methylene chloride) afforded 0.05 g of product as a oil.

The HC salt was prepared in ethyl acetate: mp 128–130° C.

Elemental analysis for $C_{24}H_{28}F_2N_2O_4.HCl$ Calc'd: C, 51.89; H, 6.08; N, 5.04 Found: C, 51.66; H, 5.91; N, 4.82

EXAMPLE 13

(1,4)-4-(5-Fluoro-1H-indol-3-yl)-1-{[2-(1H-indol-4-yloxy)-ethylamino]-methyl}-cyclohexanol A solution of 2-(1H-indol-4-yloxy)-ethylamine (0.17 g, 1 mmol), 5-fluoro-3-(1-oxa-sprio[2,5]oct-6-yl)-1H-indole (0.245 g, 1 mmol) in tetrahydrofuran (10 ml) was allowed to reflux overnight and then 10% p-toluenesulfonic acid in 10 ml methanol was added to a above mixture. The mixture was allowed to reflux for 24 hours and cooled to room temperature. The solvent was removed under vacuum, the residue was neutralized with 1 N sodium hydroxide (pH=9). The mixture was extracted with nethylene-isopropanol. The organic layer was dried over anhydrous sodium sulfate and filtered. Chromatography (ethanol-hexanes-ethanol-ammonium hydroxide: 7:3:0.1:0.01) afforded 0.19 g (44%) of product as white solid.

The HC salt was prepared in ethyl acetate: mp 160° C. (decomposed).

Elemental analysis for $C_{25}H_{28}FN_3O_2 \cdot HCl$ Calc'd: C, 60.23; H, 6.77; N, 8.43 Found: C, 60.11; H, 6.38; N, 8.17

The activity of the present compounds is demonstrated by the following standard pharmacological test procedures.

The PCR cloning of the human 5-$HT_{1A}$ receptor subtype from a human genomic library has been described previously Chanda et al., *Mol. Pharmacol.*, 43:516 (1993). A stable Chinese hamster ovary cell line expressing the human 5-$HT_{1A}$ receptor subtype (5-$HT_{1A}$.CHO cells) was employed throughout this study. Cells were maintained in DMEM supplemented with 10% foetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 μL of buffer. Competition experiments were performed by using 7 concentrations of unlabelled drug and a final ligand concentration of 1.5 nM. Non-specific binding was determined in the presence of 10 μM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter presoaked for 30 minutes in 0.5% polyethyleneimine.

A protocol similar to that used by Cheetham et al., *Neuropharmacol.*, 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to Ki values using the method of Cheng and Prusoff, *Biochem. Pharmacol.*, 22:3099 (1973); Ki=IC50/((Radioligand conc.)/(1+KD)).

The [$^{35}$S]-GTPγS binding assay was similar to that used by Lazareno and Birdsall, *Br. J. Pharmacol.* 109:1120 (1993). Briefly, 5-$HT_{1A}$ cloned receptor membrane fragments (as used for 5-$HT_{1A}$ receptor binding assays) were stored at −70° C. until needed. When needed, membranes were rapidly thawed, centrifuged at 40,000×g for 10 minutes and resuspended at 4° C. for 10 minutes in assay buffer (25 nM HEPES, 3 mM $MgCl_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theophylline and 10 μM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

The compounds tested correspond to those prepared in Examples 1–13 above. The results of the procedures are set forth in Table 1.

TABLE 1

| Example No. | 5-$HT_{1A}$ (Ki, nM) | ST ($K_i$, nM,) | GTPγS ED50 (% EMax) | cAMP ED50 (EMax) |
|---|---|---|---|---|
| 1a | 306.9 | 6.76 | — | — |
| 1b | 22.4 | 6.48 | 43.0 (80 %) | 9.8 (92%) |
| 2a | 996.2 | 1.19 | — | — |
| 2b | 47.8 | 0.42 | (0%) | (0%) |
| 3a | 146.8 | 26 | — | — |
| 3b | 1.08 | 2.50 | 60.5 (62 %) | 5.2 (90%) |
| 4a | 484.4 | 18.0 | — | — |
| 4b | 18.9 | 1.12 | — | (61%) |
| 4c | 353.2 | 6.37 | — | — |
| 4d | 16.7 | 0.21 | (74.8%) | — |
| 5a | 49% @1000 nM | 13.0 | — | — |
| 5b | 19.4 | 1.52 | 137 (22%) | 0% |
| 5c | 47% @1000 nM | 0.53 | — | — |
| 5d | 24.0 | 21.35 | — | — |
| 5e | 384.6 | 2.74 | — | — |
| 5f | 10.1 | 2.6 | 346.0 (30%) | 8.1 (0%) |
| 6a | 49% @1000 nM | 1.07 | — | — |
| 6b | 23.52 | 1.53 | — | — |
| 7a | 145.8 | — | — | — |
| 7b | 18.80 | — | — | — |
| 8a | 12.7 | 1.6 | (0%) | — |
| 8b | 18.9 | 0.52 | — | 0% |
| 9a | 16% @10 nM | 1.76 | (45%) | — |
| 9b | 78.3 | 3.28 | 583 (39.5%) | — |
| 10a | 26.8 | 7.33 | 92.7 (60%) | — |
| 10b | 7% @10 nM | 1.53 | — | — |
| 11a | 0% @10 nM | 1.70 | 0 | — |
| 11b | 24.9 | 0.70 | 0 | — |
| 12 | 0% @10 nM | 0.47 | 0 | — |
| 13 | 257.3 | 21 | 31 (85%) | — |

As demonstrated by the results set forth above, the compounds of the present invention are active towards 5HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula

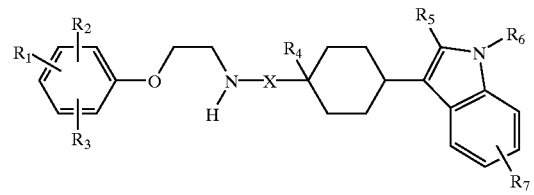

wherein:
$R_1$ and $R_2$ are each, independently, hydrogen, halogen, $CF_3$, lower alkyl, lower alkoxy, $MeSO_2$, or together can form a 5–7 membered carbocyclic or heterocyclic ring;
$R_3$ is alkoxy, halogen, hydrogen or carbamoyl;
$R_4$ is hydrogen, hydroxy, lower alkyl, or lower alkoxy;
$R_5$ is hydrogen, lower alkyl, or halogen;
$R_6$ is hydrogen, lower alkyl, or phenyl;
$R_7$ is hydrogen, lower alkyl, lower alkoxy, halogen, CN, $CF_3$, or hydroxy; and
X is $(CH_2)_n$,
wherein n is 0 to 3; or pharmaceutically acceptable salts thereof.

2. A compound as in claim 1, wherein:
$R_1$ and $R_2$ are each, independently, lower alkyl, lower alkoxy, halogen, or together can form a 5 to 7 membered carbocyclic or heterocyclic ring;
$R_3$ is alkoxy, halogen, hydrogen or carbamoyl;
$R_4$ is hydrogen or hydroxy;
$R_5$ is hydrogen;
$R_6$ is hydrogen or lower alkyl;
$R_7$ is halogen or CN; and
X is $(CH_2)_n$,
wherein n is 0 to 3; or pharmaceutically acceptable salts thereof.

3. The compound of claim 1 which is [(cis)-4-(5-Fluoro-1H-indol-3-yl)-cyclohexyl]-[2-2-methoxy-phenoxy)-ethyl]-amine.

4. The compound of claim 1 which is [(trans)-4-(5-Fluoro-1H-indol-3-yl)-cyclohexyl]-[2-(2-methoxy-phenoxy)-ethyl]-amine.

5. The compound of claim 1 which is [(1,4-cis)-4-(6-Fluoro-1H-indol-3-yl)-cyclohexyl]-[2-(5-fluoro-2-methoxy-phenoxy)-ethyl]amine.

6. The compound of claim 1 which is [(1,4-trans)-4-(6-Fluoro-1H-indol-3-yl)-cyclohexyl]-[2-(5-fluoro-2-methoxy-phenoxy)-ethyl]-amine.

7. The compound of claim 1 which is [(cis)-4-(5-Fluoro-1H-indol-3-yl)-cyclohexyl]-[2-(2-(1H-indol-4-yloxy)ethyl]-amine.

8. The compound of claim 1 which is [(trans)-4-(5-Fluoro-1H-indol-3-yl)-cyclohexyl]-[2-(2-(1H-indol-4-yloxy)ethyl]-amine.

9. The compound of claim 1 which is [(cis)-4-(1H-Indol-3-yl)-cyclohexyl]-[2-(2-(1H-indol-4-yloxy)ethyl]-amine.

10. The compound of claim 1 which is [(trans)-4-(1H-Indol-3-yl)-cyclohexyl]-[2-(2-(1H-indol-4-yloxy)ethyl]-amine.

11. The compound of claim 1 which is [2-(2,3)-Dihydro-benzo[1,4]dioxin-5-yloxy-ethyl]-[(1,4-cis)-4-(5-fluoro-1H-indol-3-yl)-cyclohexyl]-amine.

12. The compound of claim 1 which is [2,(2,3)-Dihydro-benzo[1,4]dioxin-5-yloxy-ethyl]-[(1,4-trans)-4-(5-fluoro-1H-indol-3-yl)-cyclohexyl]amine.

13. The compound of claim 1 which is [2-(2,3)-Dihydro-benzo[1,4]dioxin-5-yloxy-ethyl]-[(1,4-cis)-4-(6-fluoro-1H-indol-3-yl)-cyclohexyl]-amine.

14. The compound of claim 1 which is [2-(2,3)-Dihydro-benzo[1,4]dioxin-5-yloxy)-ethyl]-[(1,4-trans)-4-(6-fluoro-1H-indol-3-yl)-cyclohexyl]-amine.

15. The compound of claim 1 which is [2-(6-Fluorochroman-8-yloxy)-ethyl]-[(1,4-cis)-4-(5-fluoro-1H-indol-3-yl)-cyclohexyl]-amine.

16. The compound of claim 1 which is [2-(6-Fluorochroman-8-yloxy)-ethyl]-[(1,4-trans)-4-(5-fluoro-1H-indol-3-yl)-cyclohexyl]-amine.

17. The compound of claim 1 which is 3-{(1,4-cis)-4-[2-(6-Fluorochroman-8-yloxy)-ethylamino]-cyclohexyl}-1-methyl-1H-indol-5-carbonitrile.

18. The compound of claim 1 which is 3-{(1,4-cis)-4-[2-(6-Fluorochroman-8-yloxy)-ethylamino]-cyclohexyl}-1-methyl-1H-indol-5-carbonitrile.

19. The compound of claim 1 which is 3-{(1,4-trans)-4-[2-(6-Fluorochroman-8-yloxy)-ethylamino]-cyclohexyl}-1H-indol-5-carbonitrile.

20. The compound of claim 1 which is 3{(1,4-cis)-4-[2-(5-Fluoro-2,3-dihydro-benzofuran-7-yloxy)ethylamino]-cyclohexyl]}-1H-indol-5-carbonitrile.

21. The compound of claim 1 which is 3-{(1,4-trans)-4-[2-(5-Fluoro-2,3-dihydro-benzofuran-7-yloxy)ethylamino]-cyclohexyl}-1H-indol-5-carbonitrile.

22. The compound of claim 1 which is [2-(5-Fluoro-benzofuran-7-yloxy)-ethyl]-[(1,4-cis)-4-(5-fluoro-1H-indol-3-yl)-cyclohexyl]-amine.

23. The compound of claim 1 which is [2-(5-Fluoro-benzofuran-7-yloxy)-ethyl]-[(1,4-trans)-4-(5-fluoro-1H-indol-3-yl)-cyclohexyl]-amine.

24. The compound of claim 1 which is [2-(6-Chloro-1H-benzoimidazol-4-yloxy)-ethyl]-[(1,4-trans)-4-(5-fluoro-1H-indol-3-yl)-cyclohexyl]-amine.

25. The compound of claim 1 which is [2-(6-Chloro-2-methyl-1H-benzoimidazol-4-yloxy)-ethyl]-[(1,4-trans)-4-(5-fluoro-1H-indol-3-yl)-cyclohexyl]-amine.

26. The compound of claim 1 which is [(1,4-cis)-4-(5-Fluoro-1H-indol-3-yl)-cyclohexyl]-[2-(4-fluoro-2-methoxy-phenoxy)-ethyl]-amine.

27. The compound of claim 1 which is [(1,4-trans)-4-(5-Fluoro-1H-indol-3-yl)-cyclohexyl]-[2-(4-fluoro-2-methoxy-phenoxy)-ethyl]-amine.

28. The compound of claim 1 which is [(1,4-trans)-4-(5-Fluoro-1H-indol-3-yl)-cyclohexylmethyl]-[2-(2-methoxy-phenoxy)-ethyl]-amine.

29. The compound of claim 1 which is 3-(4-{[2-(methoxy-phenoxy)-ethylamino]-methyl}-cyclohexyl)-1H-indol-5-carbonitrile.

30. The compound of claim 1 which is (1,4-cis)-[2-(4,5-Difluoro-2-methoxy-phenoxy)-ethyl]-{4-(5-fluoro-1H-indol-3-yl)-cyclohexyl]-amine.

31. The compound of claim 1 which is (1,4-trans)-[2-(4,5-Difluoro-2-methoxy-phenoxy)-ethyl]-[1-(5-fluoro-1H-indol-3-yl)-cyclohexyl]-amine.

32. The compound of claim 1 which is [(1,4-trans)-4-(5-Fluoro-1H-indol-3-yl)-cyclohexyl]-[2-(5-fluoro-4-methane sulfonyl-2-methoxy-phenoxy)-ethyl]-amine.

33. The compound of claim 1 which is (1,4)-4-(5-Fluoro-1H-indol-3-yl)-1-}[2-(1H-indol-4-yloxy)-ethylamino]-methyl}-cyclohexanol.

34. A pharmaceutical composition comprising a compound of the formula:

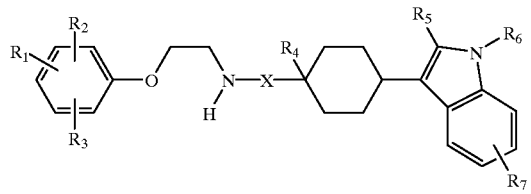

wherein:

$R_1$ and $R_2$ are each, independently, hydrogen, halogen, $CF_3$, lower alkyl, lower alkoxy, $MeSO_2$, or together can form a 5–7 membered carbocyclic or heterocyclic ring;

$R_3$ is alkoxy, halogen, hydrogen or carbamoyl;

$R_4$ is hydrogen, hydroxy, lower alkyl, or lower alkoxy;

$R_5$ is hydrogen, lower alkyl, or halogen;

$R_6$ is hydrogen, lower alkyl, or phenyl;

$R_7$ is hydrogen, lower alkyl, lower alkoxy, halogen, CN, $CF_3$, or hydroxy; and X is $(CH_2)_n$, wherein n is 0 to 3; or pharmaceutically acceptable salts thereof.

35. A method for alleviating the symptoms of depression in a patient in need thereof comprising administering to said patient an antidepressant effective amount of a compound of the formula:

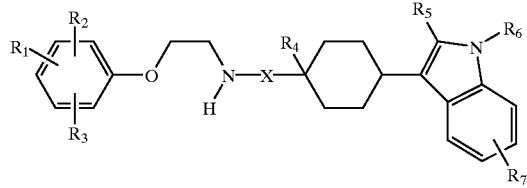

wherein:

$R_1$ and $R_2$ are each, independently, hydrogen, halogen, $CF_3$, lower alkyl, lower alkoxy, $MeSO_2$, or together can form a 5–7 membered carbocyclic or heterocyclic ring;

$R_3$ is alkoxy, halogen, hydrogen or carbamoyl;

$R_4$ is hydrogen, hydroxy, lower alkyl, or lower alkoxy;

$R_5$ is hydrogen, lower alkyl, or halogen;

$R_6$ is hydrogen, lower alkyl, or phenyl;

$R_7$ is hydrogen, lower alkyl, lower alkoxy, halogen, CN, $CF_3$, or hydroxy; and X is $(CH_2)_n$, wherein n is 0 to 3; or pharmaceutically acceptable salts thereof.

* * * * *